United States Patent
Iwasa et al.

(10) Patent No.: US 9,474,740 B2
(45) Date of Patent: Oct. 25, 2016

(54) ECTOPARASITE CONTROL AGENT

(71) Applicant: Nippon Soda Co., Ltd., Chiyoda-ku, Tokyo (JP)

(72) Inventors: Takao Iwasa, Chiyoda-ku (JP); Koichi Hirata, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/771,866

(22) PCT Filed: Feb. 28, 2014

(86) PCT No.: PCT/JP2014/055057
§ 371 (c)(1),
(2) Date: Sep. 1, 2015

(87) PCT Pub. No.: WO2014/136672
PCT Pub. Date: Sep. 12, 2014

(65) Prior Publication Data
US 2016/0008321 A1    Jan. 14, 2016

(30) Foreign Application Priority Data
Mar. 8, 2013 (JP) .................................. 2013-046259

(51) Int. Cl.
| A61K 31/382 | (2006.01) |
| A01N 43/16 | (2006.01) |
| A01N 43/18 | (2006.01) |
| A61K 31/351 | (2006.01) |
| A61K 31/381 | (2006.01) |
| A01N 43/10 | (2006.01) |
| C07D 333/36 | (2006.01) |
| C07D 335/02 | (2006.01) |

(52) U.S. Cl.
CPC ............. *A61K 31/382* (2013.01); *A01N 43/10* (2013.01); *A01N 43/16* (2013.01); *A01N 43/18* (2013.01); *A61K 31/351* (2013.01); *A61K 31/381* (2013.01); *C07D 333/36* (2013.01); *C07D 335/02* (2013.01)

(58) Field of Classification Search
CPC .................................................. A61K 31/382
USPC ......................................................... 549/28
See application file for complete search history.

(56) References Cited

U.S. PATENT DOCUMENTS

| 2011/0251388 A1 | 10/2011 | Kutose et al. |
| 2012/0225895 A1 | 9/2012 | Takahashi et al. |
| 2013/0310254 A1 | 11/2013 | Werner et al. |

FOREIGN PATENT DOCUMENTS

| JP | 2012-092091 A | 5/2012 |
| WO | WO 2010/070910 A1 | 6/2010 |
| WO | WO 2011/058963 A1 | 5/2011 |
| WO | WO 2012/072489 A1 | 6/2012 |

OTHER PUBLICATIONS

International Search Report dated Apr. 1, 2014, in PCT/JP2014/055057.

*Primary Examiner* — Taofiq A Solola
(74) *Attorney, Agent, or Firm* — Foley & Lardner LLP

(57) ABSTRACT

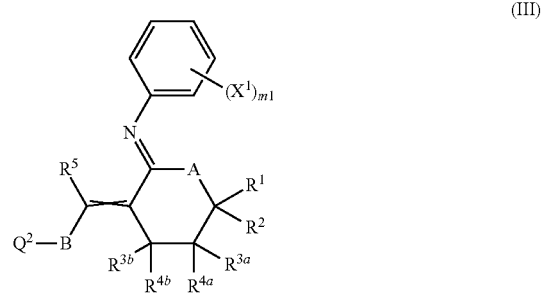

wherein, in formula (III), $X^1$ represents a C1-6 alkyl group which is unsubstituted or has a substituent, or other groups; m1 represents any integer of 0 to 5; A represents an oxygen atom or a sulfur atom; each of $R^1$ and $R^2$ independently represents a hydrogen atom, a C1-6 alkyl group which is unsubstituted or has a substituent, or other groups; $R^5$ represents a hydrogen atom or a C1-6 alkyl group which is unsubstituted or has a substituent; B represents an oxygen atom or a sulfur atom; $Q^2$ represents a C7-11 aralkyl group which is unsubstituted or has a substituent $X^2$, or other groups; and each of $R^{3a}$, $R^{3b}$, $R^{4a}$, and $R^{4b}$ independently represents a hydrogen atom, a C1-6 alkyl group which is unsubstituted or has a substituent, or other groups.

9 Claims, No Drawings

ECTOPARASITE CONTROL AGENT

TECHNICAL FIELD

The present invention relates to an ectoparasite control agent having a reliable effect.

This application is a National Stage application of PCT/JP2014/055057, filed Feb. 28, 2014, which claims priority from Japanese Patent Application No. 2013-046259, filed Mar. 8, 2013, the content of which is incorporated herein by reference.

BACKGROUND ART

Ectoparasites such as fleas, lice, flies, mosquitoes, ticks, and mites, and endoparasites such as digestive tract nematodes, trematodes, and heartworms are problematic to both humans and animals. Such parasites include an egg stage, a larval stage, a pupal stage, a nymph stage, and an adult stage, decrease the body weight increase of a host, cause low quality of leather, wool, and meat, cause death in some cases, and exert a serious influence on productivity in the domestic animal industry. In addition, ectoparasites and endoparasites spread disease through food or pets, and cause discomfort. In particular, it is known that ectoparasites cause infection by becoming the habitat for various microbial pathogens including bacteria, viruses, and parasitic protozoa. Many ectoparasites are pathogenic with respect to humans, and other homoiothermal mammals and birds. Examples of diseases in which ectoparasites are involved include malaria, lymphatic filariasis, and blood-borne filariasis, trachoma, trypanosomiasis, leishmaniasis, Rocky Mountain spotted fever, Lyme disease, babesiosis, and food-borne diseases caused by *salmonella*, *E. coli*, or *Campylobacter*, but the examples thereof are not limited thereto.

An important point in medical care against parasite by parasite exterminating drugs is to promote the development of a reagent capable of suppressing the parasite. For example, usual methods for suppressing parasite by parasite exterminating drugs, in general, focus on the use of an agricultural pesticide, and these are unsuccessful or insufficient in many cases for at least one of the reasons described below. The reasons are (1) the owner or the applicator's compliance (frequent administration is required) failure, (2) behavior or physiological intolerance of an animal with respect to the exterminator product or the administration method, (3) expression of resistance of ectoparasites with respect to a reagent, or (4) a negative effect with respect to the environment and/or toxicity.

Specifically, it is known or considered that ticks and fleas are parasitic on wild animals in the same manner as on domestic animals or humans, and are involved in mediating pathogens including bacteria, viruses, and parasitic protozoa. Currently, ticks are considered to be the second most common vectors of human diseases in the world after mosquitoes; however, in North America, ticks are considered to be the most serious pathogens. Since there is often a need to treat the environmental reservoir host together with the direct host at the same time, effective extermination against parasite by ectoparasites such as fleas in the domestic environment is difficult and unrealistic in many cases. Currently, suppression of ticks in the agricultural environment is performed by an overall harmful organism treatment method in which various suppression methods are adapted to one region or one type of tick, while sufficiently considering the environmental effect.

Although the use of insecticides and exterminators is beneficial to suppress ectoparasites, improved compounds, formulations, and methods to replace the existing ones are needed. Desirable compounds, formulations, and methods will not only provide alternative treatments but also overcome at least some of the restrictions of current methods. Such restrictions include toxicity and safety to an animal, a user, or an owner, restrictions relating to the efficacy (potency, durability of activity, killing speed), and the problem of resistance (limited to this). In addition, affecting the beneficial use of insecticides and exterminators is hindrance of administration, and as such hindrance, the method, a user or an owner's compliance problem relating to the treatment recommendation, and repetition of administrations are exemplified. For example, excessively repeatedly treating animals is often troublesome and difficult for a user or an owner, and therefore, it is desirable to reduce the number of administrations while maintaining the efficacy.

Specific examples of the 1-heterodiene compounds used in the ectoparasite control agent of the present invention are disclosed in PTLs 1 and 2.

CITATION LIST

Patent Literature

[PTL 1] PCT international Publication No. WO2010/070910
[PTL 2] PCT international Publication No. WO2011/058963

SUMMARY OF INVENTION

Technical Problem

An object of the ectoparasite control agent according to the present invention is to overcome at least some of the restrictions when using an insecticide or an exterminator currently used, in particular, the restrictions relating to a killing speed, a long validity period, or suppression of ectoparasites such as mites and ticks.

Solution to Problem

In order to solve the above problems, the present inventors conducted thorough research. As a result, they found that 1-heterodiene compounds having a specific structure or salts thereof are useful as an effective component of the ectoparasite control agent. The present invention has been completed by further consideration on the basis of these findings.

That is, the present invention includes the following.

[1] An ectoparasite control agent, including, as an effective component: at least one compound selected from 1-heterodiene compounds represented by Formula (I) and salts thereof:

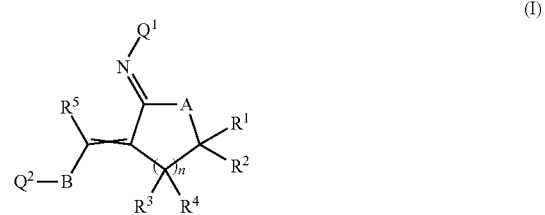

wherein, in Formula (I), $Q^1$ represents a C6-10 aryl group which is unsubstituted or has a substituent $X^1$, or a 5- or 6-membered heteroaryl group which is unsubstituted or has a substituent $X^1$;

$X^1$ represents a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a hydroxyl group, a C1-6 alkoxy group which is unsubstituted or has a substituent, a C1-7 acyl group which is unsubstituted or has a substituent, a C1-6 alkoxycarbonyl group which is unsubstituted or has a substituent, an amino group which is unsubstituted or has a substituent, a C1-6 alkylthio group which is unsubstituted or has a substituent, a C1-6 alkylsulfonyl group which is unsubstituted or has a substituent, a C6-10 aryl group which is unsubstituted or has a substituent, a 3- to 6-membered heterocyclic group which is unsubstituted or has a substituent, a halogeno group, a cyano group, or a nitro group;

the number of the substituent $X^1$ on $Q^1$ is any integer of 1 to 5; and when the number of the substituent $X^1$ is 2 or greater, $X^1$s may be the same as or different from each other;

A represents an oxygen atom or a sulfur atom;

each of $R^1$ and $R^2$ independently represents a hydrogen atom, a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a C6-10 aryl group which is unsubstituted or has a substituent, a 3- to 6-membered heterocyclic group which is unsubstituted or has a substituent, or a cyano group;

an exomethylene group which is unsubstituted or has a substituent may be formed by $R^1$ and $R^2$ being taken together;

each of $R^3$ and $R^4$ independently represents a hydrogen atom, a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a C6-10 aryl group which is unsubstituted or has a substituent, a 3- to 6-membered heterocyclic group which is unsubstituted or has a substituent, a halogeno group, or a cyano group;

n represents the number of methylene substituted with $R^3$ and $R^4$, and is any integer of 1 to 4; and when n is 2 or greater, $R^3$ and $R^4$ may be the same as or different from each other;

$R^3$ and $R^4$ may be connected to each other and form a ring together with the carbon atom to which $R^3$ and $R^4$ are bonded;

$R^5$ represents a hydrogen atom or a C1-6 alkyl group which is unsubstituted or has a substituent;

B represents an oxygen atom or a sulfur atom;

$Q^2$ represents a C7-11 aralkyl group which is unsubstituted or has a substituent $X^2$, a C6-10 aryl group which is unsubstituted or has a substituent $X^2$, or a 5- or 6-membered heteroaryl group which is unsubstituted or has a substituent $X^2$;

$X^2$ represents a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a hydroxyl group, a C1-6 alkoxy group which is unsubstituted or has a substituent, a C1-7 acyl group which is unsubstituted or has a substituent, a C1-6 alkoxycarbonyl group which is unsubstituted or has a substituent, an amino group which is unsubstituted or has a substituent, a C1-6 alkylthio group which is unsubstituted or has a substituent, a C1-6 alkylsulfonyl group which is unsubstituted or has a substituent, a C6-10 aryl group which is unsubstituted or has a substituent, a 3- to 6-membered heterocyclic group which is unsubstituted or has a substituent, a halogeno group, a cyano group, or a nitro group;

the number of the substituent $X^2$ on $Q^2$ is any integer of 1-5; and when the number of the substituent $X^2$ is 2 or greater, $X^2$s may be the same as or different from each other; and according to the stereoisomerism of the double bond to which $R^5$ and B are bonded in Formula (I), the compound shows (E), (Z), or (E/Z).

[2] The ectoparasite control agent according to [1], in which the compounds represented by Formula (I) are compounds represented by Formula (II):

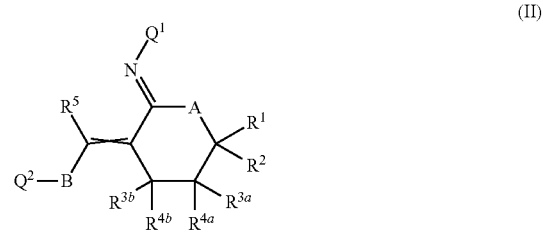

(II)

wherein, in Formula (II), each of $Q^1$, A, $R^1$, $R^2$, $R^5$, B, and $Q^2$ has the same definition as that in Formula (I);

each of $R^{3a}$, $R^{3b}$, $R^{4a}$, and $R^{4b}$ independently represents a hydrogen atom, a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a C6-10 aryl group which is unsubstituted or has a substituent, a 3- to 6-membered heterocyclic group which is unsubstituted or has a substituent, a halogeno group, or a cyano group; and $R^{3a}$ and $R^{4a}$ may be connected to each other and form a ring together with the carbon atom to which $R^{3a}$ and $R^{4a}$ are bonded.

[3] The ectoparasite control agent according to [1], in which the compounds represented by Formula (I) are compounds represented by Formula (III):

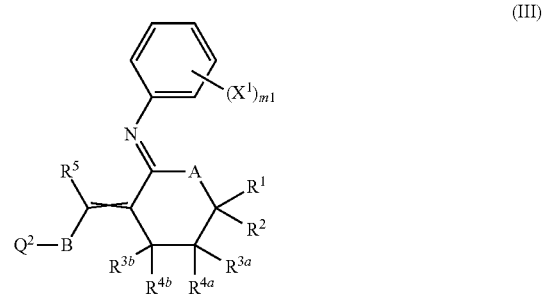

(III)

wherein, in Formula (III), each of $X^1$, A, $R^1$, $R^2$, $R^5$, B, and $Q^2$ has the same definition as that in Formula (I);

m1 represents any integer of 0 to 5;

each of $R^{3a}$, $R^{3b}$, $R^{4a}$, and $R^{4b}$ independently represents a hydrogen atom, a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a C6-10 aryl group which is unsubstituted or has a substituent, a 3- to 6-membered heterocyclic group which is unsubstituted or has a substituent, a halogeno group, or a cyano group; and $R^{3a}$ and $R^{4a}$ may be connected to each other and form a ring together with the carbon atom to which $R^{3a}$ and $R^{4a}$ are bonded.

[4] A formulation, including at least one compound selected from the 1-heterodiene compounds and salts thereof according to any one of [1] to [3]; and at least one acceptable carrier.

[5] The formulation according to [4], further including: at least one additional effective component.

[6] The formulation according to [4], which is a pharmaceutical formulation for humans.

[7] The formulation according to [4], which is a pharmaceutical formulation for animals.

[8] A method for suppressing parasites in the body or on the body surface of an animal requiring suppression of parasite by parasites, in which an effective amount of at least one compound selected from the 1-heterodiene compounds and salts thereof according to any one of [1] to [3] is administered to the animal.

[9] The method according to [8], in which at least one other effective component is administered to the animal.

[10] The method according to [8], in which the animal is a human.

[11] The method according to [8], in which the animal is a pet.

[12] The method according to [11], in which the pet is a dog or a cat.

[13] The method according to [8], in which the animal is livestock.

[14] The method according to [8], in which the parasite is a tick.

[15] A method for preventing or treating diseases infected through parasites, in which an effective amount of at least one compound selected from the 1-heterodiene compounds and salts thereof according to any one of [1] to [3] is administered to an animal in need thereof.

[16] The method according to [15], in which at least one other effective component is administered to the animal.

[17] The method according to [15], in which the animal is a human.

[18] The method according to [15], in which the animal is a pet.

[19] The method according to [18], in which the pet is a dog or a cat.

[20] The method according to [15], in which the animal is livestock.

[21] The method according to [15], in which the parasite is a tick.

[22] A method for suppressing harmful organisms, in which at least one compound selected from the 1-heterodiene compounds and salts thereof according to any one of [1] to [3] acts on the harmful organisms and/or the habitat thereof.

[23] The method according to [22], in which the habitat is an animal.

[24] A use of at least one compound selected from the 1-heterodiene compounds and salts thereof according to any one of [1] to [3] for suppressing harmful organisms.

[25] A use of at least one compound selected from the 1-heterodiene compounds and salts thereof according to any one of [1] to [3] for treating.

[26] A use of at least one compound selected from the 1-heterodiene compounds and salts thereof according to any one of [1] to [3] for suppressing parasite by ectoparasites.

Advantageous Effects of Invention

The ectoparasite control agent according to the present invention contains a parasite-exterminating compound used in the body or on the body surface of an animal, a method, and a formulation, and provides an alternative for handling parasite of parasite extermination, in particular, parasite of ectoparasite extermination to a pet. In addition, the ectoparasite control agent according to the present invention can overcome at least some of the restrictions when using an insecticide or an exterminator currently used, in particular, the restrictions relating to a killing speed, a long validity period, or suppression of ectoparasites such as mites and ticks.

DESCRIPTION OF EMBODIMENTS

Hereinafter, preferable examples of the present invention will be described, but the present invention is not limited to the examples. Additions, omissions, substitutions, and other modifications can be made to the configuration of the present invention without departing from the spirit or scope of the present invention.

The ectoparasite control agent of the present invention contains at least one compound selected from the 1-heterodiene compounds (hereinafter, also referred to as the compound (1)) represented by Formula (I) and salts thereof as an effective component.

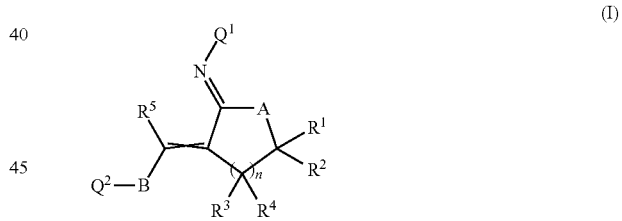

(I)

First, the term "unsubstituted" in the present invention means that only a group which is a base skeleton is present. When only the name of a group which is a base skeleton is described without describing "have a substituent", it means "unsubstituted" unless specified otherwise.

On the other hand, the term "have a substituent" means that any hydrogen atom of a group which is a base skeleton is substituted with a group having the same structure as or different from the base skeleton. Therefore, "a substituent" is another group which is bonded to a group which is a base skeleton. The substituent may be one, or two or more. Two or more substituents may be the same as or different from each other.

The term "C1-6" represents that the carbon atom number of a group which is a base skeleton is 1 to 6. The carbon atom number does not include the number of carbon atoms present in a substituent. For example, a butyl group having an ethoxy group as a substituent is classified as a C2 alkoxy C4 alkyl group.

"Substituent" is not particularly limited as long as it is chemically acceptable and has the effect of the present invention. Hereinafter, groups which can be a "substituent" are exemplified.

C1-6 alkyl groups such as a methyl group, an ethyl group, an n-propyl group, an i-propyl group, an n-butyl group, an s-butyl group, an i-butyl group, a t-butyl group, an n-pentyl group, and an n-hexyl group;

C2-6 alkenyl groups such as a vinyl group, a 1-propenyl group, a 2-propenyl group (allyl group), a 1-butenyl group, a 2-butenyl group, a 3-butenyl group, a 1-methyl-2-propenyl group, and a 2-methyl-2-propenyl group;

C2-6 alkynyl groups such as an ethynyl group, a 1-propynyl group, a 2-propynyl group, a 1-butynyl group, a 2-butynyl group, a 3-butynyl group, and a 1-methyl-2-propynyl group;

C3-8 cycloalkyl groups such as a cyclopropyl group, a cyclobutyl group, a cyclopentyl group, and a cyclohexyl group;

C4-8 cyclo alkenyl groups such as a 2-cyclopentenyl group, a 3-cyclohexenyl group, and a 4-cyclooctenyl group.

C6-10 aryl groups such as a phenyl group and a naphthyl group;

C7-11 aralkyl groups such as a benzyl group and a phenethyl group;

saturated heterocyclic groups such as an aziridinyl group, an oxiranyl group, an azetidinyl group, an oxetanyl group, a pyrrolidinyl group, a tetrahydrofuranyl group, a piperidyl group, a piperazinyl group, a morpholinyl group, a dioxolanyl group, and a dioxanyl group;

5-membered heteroaryl groups such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group;

6-membered heteroaryl groups such as a pyridyl group, a pyrazinyl group, a pyrimidinyl group, a pyridazinyl group, and a triazinyl group;

C1-7 acyl groups such as a formyl group, an acetyl group, a propionyl group, a benzoyl group, and a cyclohexyl carbonyl group;

a hydroxyl group;

C1-6 alkoxy groups such as a methoxy group, an ethoxy group, an n-propoxy group, an i-propoxy group, an n-butoxy group, an s-butoxy group, an i-butoxy group, and a t-butoxy group;

C2-6 alkenyloxy groups such as a vinyloxy group, an allyloxy group, a propenyloxy group, and a butenyloxy group;

C2-6 alkynyloxy groups such as an ethynyloxy group and a propargyloxy group;

C6-10 aryloxy groups such as a phenoxy group and a 1-naphthoxy group;

C7-11 aralkyloxy groups such as a benzyloxy group and a phenethyloxy group;

C1-7 acyloxy groups such as a formyloxy group, an acetyloxy group, a propionyloxy group, a benzoyloxy group, and a cyclohexyl carbonyloxy group;

C1-6 alkoxy carbonyl groups such as a methoxycarbonyl group, an ethoxy carbonyl group, an n-propoxycarbonyl group, an i-propoxycarbonyl group, an n-butoxycarbonyl group, and a t-butoxycarbonyl group;

a carboxyl group;

halogeno groups such as a fluoro group, a chloro group, a bromo group, and an iodo group;

C1-6 haloalkyl groups such as a chloromethyl group, a chloroethyl group, a trifluoromethyl group, a 1,2-dichloro-n-propyl group, a 1-fluoro-n-butyl group, and a perfluoro-n-pentyl group;

C2-6 haloalkenyl groups such as a 2-chloro-1-propenyl group and a 2-fluoro-1-butenyl group;

C2-6 haloalkynyl groups such as a 4,4-dichloro-1-butynyl group, a 4-fluoro-1-pentynyl group, and a 5-bromo-2-pentynyl group;

C6-10 haloaryl groups such as a 4-chlorophenyl group, a 4-fluorophenyl group, and a 2,4-dichlorophenyl group;

C1-6 haloalkoxy groups such as a trifluoromethoxy group, a 2-chloro-n-propoxy group, and a 2,3-dichlorobutoxy group;

C2-6 haloalkenyloxy groups such as a 2-chloropropenyloxy group and a 3-bromobutenyloxy group;

C6-10 haloaryloxy groups such as a 4-fluorophenyloxy group and a 4-chloro-1-naphthoxy group;

C1-7 haloacyl groups such as a chloroacetyl group, a trifluoroacetyl group, a trichloroacetyl group, and a 4-chlorobenzoyl group;

an amino group;

C1-6 alkyl amino groups such as a methyl amino group, a dimethyl amino group, and a diethyl amino group;

C6-10 aryl amino groups such as an anilino group and a naphthyl amino group;

C7-11 aralkyl amino groups such as a benzyl amino group and a phenethyl amino group;

C1-7 acyl amino groups such as a formyl amino group, an acetyl amino group, a propanoyl amino group, a butyryl amino group, an i-propylcarbonyl amino group, and a benzoyl amino group;

C1-6 alkoxycarbonyl amino groups such as a methoxycarbonyl amino group, an ethoxycarbonyl amino group, an n-propoxycarbonyl amino group, and an i-propoxycarbonyl amino group;

amino carbonyl groups which are unsubstituted or have a substituent, such as an amino carbonyl group, a dimethyl amino carbonyl group, a phenyl amino carbonyl group, and an N-phenyl-N-methyl amino carbonyl group;

C1-6 alkyl groups substituted with an imino group, such as an iminomethyl group, a (1-imino)ethyl group, and a (1-imino)-n-propyl group;

C1-6 alkyl groups substituted with a hydroxyimino group which is unsubstituted or has a substituent, such as a hydroxyiminomethyl group, a (1-hydroxyimino)ethyl group, a (1-hydroxyimino)propyl group, a methoxyiminomethyl group, and a (1-methoxyimino)ethyl group;

a mercapto group;

C1-6 alkylthio groups such as a methylthio group, an ethylthio group, an n-propylthio group, an i-propylthio group, an n-butylthio group, an i-butylthio group, an s-butylthio group, and a t-butylthio group;

C6-10 arylthio groups such as a phenylthio group and a naphthylthio group;

heteroarylthio groups such as a thiazolylthio group and a pyridylthio group;

C7-11 aralkylthio groups such as a benzylthio group and a phenethylthio group;

C1-6 alkylsulfonyl groups such as a methylsulfonyl group, an ethylsulfonyl group, and a t-butylsulfonyl group;

C6-10 arylsulfonyl groups such as a phenylsulfonyl group;

heteroaryl sulfonyl groups such as a thiazolylsulfonyl group and a pyridylsulfonyl group;

C7-11 aralkylsulfonyl groups such as a benzylsulfonyl group and a phenethylsulfonyl group;

tri C1-6 alkyl substituted silyl groups such as a trimethylsilyl group, a triethylsilyl group, and a t-butyldimethylsilyl group;

triaryl substituted silyl groups such as a triphenylsilyl group; and a cyano group; and a nitro group; and in addition, in these "substituents", any hydrogen atom in the substituent may be substituted with a group having a different structure.

$Q^1$ represents a C6-10 aryl group which is unsubstituted or has a substituent $X^1$, or a 5- or 6-membered heteroaryl group which is unsubstituted or has a substituent $X^1$.

The number of the substituent $X^1$ on $Q^1$ is any integer of 1 to 5. When the number of the substituent $X^1$ is 2 or greater, $X^1$s may be the same as or different from each other.

A preferable number of the substituent $X^1$ is any integer of 1 and 2.

The "C6-10 aryl group" in $Q^1$ may be any one of a monocyclic aryl group and a polycyclic aryl group. In the polycyclic aryl group, if at least one ring is an aromatic ring, the remaining ring may be any one of a saturated alicycle, an unsaturated alicycle, and an aromatic ring.

Examples of the "C6-10 aryl group" include a phenyl group, a naphthyl group, an azulenyl group, an indenyl group, an indanyl group, and a tetralinyl group.

The "5- to 6-membered heteroaryl group" in $Q^1$ includes 1 to 4 heteroatoms selected from the group consisting of a nitrogen atom, an oxygen atom, and a sulfur atom as a configuration atom of a ring.

Examples of the 5-membered heteroaryl ring can include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group.

Examples of the 6-membered heteroaryl ring can include a pyridyl group, a pyrazinyl group, a pyrimidinyl group, a pyridazinyl group, and a triazinyl group.

Examples of preferable $Q^1$ can include a phenyl group.

$X^1$ represents a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a hydroxyl group, a C1-6 alkoxy group which is unsubstituted or has a substituent, a C1-7 acyl group which is unsubstituted or has a substituent, a C1-6 alkoxycarbonyl group which is unsubstituted or has a substituent, an amino group which is unsubstituted or has a substituent, a C1-6 alkylthio group which is unsubstituted or has a substituent, a C1-6 alkylsulfonyl group which is unsubstituted or has a substituent, a C6-10 aryl group which is unsubstituted or has a substituent, a 3- to 6-membered heterocyclic group which is unsubstituted or has a substituent, a halogeno group, a cyano group, or a nitro group.

The "C1-6 alkyl group" in $X^1$ may be linear or branched. Examples of the alkyl group can include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group, and an i-hexyl group.

Examples of the "C1-6 alkyl group which has a substituent" can include C3-8 cycloalkyl C1-6 alkyl groups such as a cyclopropylmethyl group, a 2-cyclopropylethyl group, a cyclopentylmethyl group, a 2-cyclohexylethyl group, and a 2-cyclooctyl ethyl group;

C1-6 haloalkyl groups such as a fluoromethyl group, a chloromethyl group, a bromomethyl group, a difluoromethyl group, a dichloromethyl group, a dibromomethyl group, a trifluoromethyl group, a trichloromethyl group, a tribromomethyl group, a 2,2,2-trifluoroethyl group, a 2,2,2-trichloroethyl group, a pentafluoroethyl group, a 4-fluorobutyl group, a 4-chlorobutyl group, a 3,3,3-trifluoropropyl group, a 2,2,2-trifluoro-1-trifluoromethylethyl group, a perfluorohexyl group, a perchlorohexyl group, and a 2,4,6-trichlorohexyl group;

hydroxy C1-6 alkyl groups such as a hydroxymethyl group and a 2-hydroxyethyl group;

C1-6 alkoxy C1-6 alkyl groups such as a methoxymethyl group, an ethoxymethyl group, a methoxyethyl group, an ethoxyethyl group, a methoxy-n-propyl group, an ethoxymethyl group, an ethoxyethyl group, an n-propoxymethyl group, an i-propoxyethyl group, an s-butoxymethyl group, and a t-butoxyethyl group;

C2-6 alkenyloxy C1-6 alkyl groups such as a vinyloxymethyl group, an allyloxymethyl group, a propenyloxymethyl group, and a butenyloxymethyl group;

heteroaryloxy C1-6 alkyl groups such as a pyridin-2-yloxy methyl group;

C1-7 acyl 1-6 alkyl groups such as a formylmethyl group, an acetylmethyl group, and a propionylmethyl group;

C1-7 acyloxy C1-6 alkyl groups such as a formyloxymethyl group, an acetoxymethyl group, a 2-acetoxyethyl group, a propionyloxymethyl group, and a propionyloxyethyl group;

carboxyl group C1-6 alkyl groups such as a carboxylmethyl group and a carboxylethyl group;

C1-6 alkoxy carbonyl C1-6 alkyl groups such as a methoxycarbonyl methyl group, an ethoxy carbonyl methyl group, an n-propoxycarbonyl methyl group, and an i-propoxycarbonyl methyl group;

C1-7 acyl amino C1-6 alkyl groups such as a formamidomethyl group, an acetamidomethyl group, a 2-acetamidoethyl group, a propionyl amino methyl group, and a propionyl amino ethyl group;

C1-6 alkyl amino carbonyl C1-6 alkyl groups such as a methyl amino carbonyl methyl group, an ethyl amino carbonyl methyl group, an i-propyl amino carbonyl methyl group, a t-butyl amino carbonyl methyl group, an s-butyl amino carbonyl methyl group, and an n-pentyl amino carbonyl methyl group;

C1-6 alkoxy carbonyl amino C1-6 alkyl groups such as a methoxycarbonyl amino methyl group, an ethoxycarbonyl amino methyl group, an i-propoxycarbonyl amino methyl group, a t-butoxycarbonyl amino methyl group, an s-butyloxycarbonyl amino methyl group, and an n-pentyloxycarbonyl amino methyl group;

C7-11 aralkyl groups such as a benzyl group and a phenethyl group; and

C6-10 aryl carbonyl amino C1-6 alkyl groups such as a benzoyl amino methyl group.

Examples of the "C2-6 alkenyl group" in $X^1$ can include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group.

Examples of the "C2-6 alkenyl group which has a substituent" can include C2-6 haloalkenyl groups such as a 2-chloro-1-propenyl group and a 2-fluoro-1-butenyl group.

Examples of the "C2-6 alkynyl group" in X¹ can include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group.

Examples of the "C2-6 alkynyl group which has a substituent" can include C2-6 haloalkynyl groups such as a 4,4-dichloro-1-butynyl group, a 4-fluoro-1-pentynyl group, and a 5-bromo-2-pentynyl group.

Examples of the "C3-8 cycloalkyl group" in X¹ can include a cyclopropyl group, a cyclobutyl group, a cyclopentyl group, a cyclohexyl group, and a cycloheptyl group.

Examples of the "C1-6 alkoxy group" in X¹ can include a methoxy group, an ethoxy group, an n-propoxy group, an n-butoxy group, an n-pentyloxy group, an n-hexyloxy group, an i-propoxy group, an i-butoxy group, an s-butoxy group, a t-butoxy group, and an i-hexyloxy group.

Examples of the "C1-6 alkoxy group which has a substituent" can include C1-6 haloalkoxy groups such as a chloromethoxy group, a dichloromethoxy group, a difluoromethoxy group, a trichloromethoxy group, a trifluoromethoxy group, a 1-fluoroethoxy group, a 1,1-difluoroethoxy group, a 2,2,2-trifluoroethoxy group, and a pentafluoroethoxy group.

Examples of the "C1-7 acyl group" in X¹ can include a formyl group, an acetyl group, a propionyl group, and a benzoyl group.

Examples of the "C1-7 acyl group which has a substituent" can include C1-7 haloacyl groups such as a chloroacetyl group, a trifluoroacetyl group, a trichloroacetyl group, and a 4-chlorobenzoyl group.

Examples of the "C1-6 alkoxy carbonyl group" in X¹ can include a methoxycarbonyl group, an ethoxycarbonyl group, an n-propoxycarbonyl group, and an i-propoxycarbonyl group.

Examples of the "C1-6 alkoxycarbonyl group which has a substituent" can include C3-8 cycloalkyl C1-6 alkoxy carbonyl groups such as a cyclopropyl methoxycarbonyl group, a cyclobutyl methoxycarbonyl group, a cyclopentyl methoxycarbonyl group, a cyclohexyl methoxycarbonyl group, a 2-methyl cyclopropyl methoxycarbonyl group, a 2,3-dimethyl cyclopropyl methoxycarbonyl group, a 2-chlorocyclopropyl methoxycarbonyl group, and a 2-cyclopropyl ethoxycarbonyl group; and C1-6 haloalkoxy carbonyl groups such as a fluoromethoxycarbonyl group, a chloromethoxycarbonyl group, a bromomethoxycarbonyl group, a difluoromethoxycarbonyl group, a dichloromethoxycarbonyl group, a dibromomethoxycarbonyl group, a trifluoromethoxycarbonyl group, a trichloromethoxycarbonyl group, a tribromomethoxycarbonyl group, a 2,2,2-trifluoroethoxycarbonyl group, a 2,2,2-trichloroethoxycarbonyl group, a pentafluoroethoxycarbonyl group, a 4-fluorobutoxycarbonyl group, a 3,3,3-trifluoropropoxycarbonyl group, a 2,2,2-trifluoro-1-trifluoromethyl ethoxycarbonyl group, and a perfluorohexyloxy carbonyl group.

Examples of the "amino group which has a substituent" in X¹ can include C1-6 alkyl substituted amino groups such as a methylamino group, a dimethylamino group, and a diethylamino group.

Examples of the "C1-6 alkylthio group" in X¹ can include a methylthio group, an ethylthio group, an n-propylthio group, an n-butylthio group, an n-pentylthio group, an n-hexylthio group, and an i-propylthio group.

Examples of the "C1-6 alkylsulfonyl group" in X¹ can include a methylsulfonyl group, an ethylsulfonyl group, and a t-butylsulfonyl group.

The "C6-10 aryl group" in X¹ may be any one of a monocyclic aryl group and a polycyclic aryl group. In the polycyclic aryl group, if at least one ring is an aromatic ring, the remaining ring may be any one of a saturated alicycle, an unsaturated alicycle, and an aromatic ring.

Examples of the "C6-10 aryl group" include a phenyl group, a naphthyl group, an azulenyl group, an indenyl group, an indanyl group, and a tetralinyl group.

The "3- to 6-membered heterocyclic group" in X¹ includes 1 to 4 heteroatoms selected from the group consisting of a nitrogen atom, an oxygen atom, and a sulfur atom as a configuration atom of a ring. The heterocyclic group may be any one of a monocyclic group or a polycyclic group. In the polycyclic heterocyclic group, if at least one ring is heterocyclic, the remaining ring may be any one of a saturated alicyclic, an unsaturated alicyclic, and an aromatic ring. Examples of the 3- to 6-membered heterocyclic group can include a 3- to 6-membered saturated heterocyclic group, a 5- or 6-membered heteroaryl group, and a 5- or 6-membered partially unsaturated heterocyclic group.

Examples of the 3- to 6-membered saturated heterocyclic group can include an aziridinyl group, an oxiranyl group, azetidinyl, an oxetanyl group, a pyrrolidinyl group, a tetrahydrofuranyl group, a piperidyl group, a piperazinyl group, a morpholinyl group, a dioxolanyl group, and a dioxanyl group.

Examples of the 5-membered heteroaryl group can include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group.

Examples of the 6-membered heteroaryl group can include a pyridyl group, a pyrazinyl group, a pyrimidinyl group, a pyridazinyl, and a triazinyl group.

Examples of the partially unsaturated 5-membered heterocyclic group can include a pyrrolinyl group, an imidazolinyl group (dihydroimidazolinyl group), a pyrazolinyl group, an oxazolinyl group, an isoxazolinyl group, and a thiazolinyl group.

Examples of the partially unsaturated 6-membered heterocyclic group can include a thiopyranyl group, a 2H-pyridin-1-yl group, and a 4H-pyridin-1-yl group.

Examples of the substituent on the "C6-10 aryl group" or the "3- to 6-membered heterocyclic group" can include a C1-6 alkyl group, a hydroxyl group, a C1-6 alkoxy group, a halogeno group, a cyano group, and a nitro group.

Examples of the "halogeno group" in X¹ can include a fluoro group, a chloro group, a bromo group, and an iodo group.

Examples of a preferable X¹ can include a "C1-6 alkyl group", a "C1-6 alkoxy group", "C1-6 haloalkyl group", and "a halogeno group".

A represents an oxygen atom or a sulfur atom. Preferably, A is a sulfur atom.

Each of $R^1$ and $R^2$ independently represents a hydrogen atom, a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a C6-10 aryl group which is unsubstituted or has a substituent, a 3- to 6-membered heterocyclic group which is unsubstituted or has a substituent, or a cyano group.

Here, $R^1$ and $R^2$ together may form an exomethylene group which is unsubstituted or has a substituent.

Examples of the "C1-6 alkyl group", the "C2-6 alkenyl group", the "C2-6 alkynyl group", the "C3-8 cycloalkyl group", the "C6-10 aryl group", and the "3- to 6-membered heterocyclic group", in $R^1$ and $R^2$, and a group having a substituent in these groups can include the same groups as those exemplified in $X^1$.

Preferably, each of $R^1$ and $R^2$ independently is a hydrogen atom, a C1-6 alkyl group, or a C6-10 aryl group.

More preferably, each of $R^1$ and $R^2$ is a "C1-6 alkyl group".

Examples of the "exomethylene group which has a substituent" that $R^1$ and $R^2$ together form together with the carbon atom to which $R^1$ and $R^2$ are bonded can include C1-6 alkyl substituted exomethylenes such as an ethylidene group and an isopropylidene group.

Preferably, the "exomethylene group which has a substituent" that $R^1$ and $R^2$ together form together with the carbon atom to which $R^1$ and $R^2$ are bonded is an isopropylidene group.

Each of $R^3$ and $R^4$ independently represents a hydrogen atom, a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a C6-10 aryl group which is unsubstituted or has a substituent, a 3- to 6-membered heterocyclic group which is unsubstituted or has a substituent, a halogeno group, or a cyano group.

n represents the number of methylene substituted with $R^3$ and $R^4$, and is any integer of 1 to 4. When n is 2 or greater, $R^3$ and $R^4$ may be the same as or different from each other.

Preferably, n is 1 or 2.

Examples of the "C1-6 alkyl group", the "C2-6 alkenyl group", the "C2-6 alkynyl group", the "C3-8 cycloalkyl group", the "C6-10 aryl group", the "3- to 6-membered heterocyclic group", and the "halogeno group", in $R^3$ and $R^4$, and a group having a substituent in these groups can include the same groups as those exemplified in $X^1$.

Preferably, each of $R^3$ and $R^4$ independently is a hydrogen atom or a C1-6 alkyl group.

$R^3$ and $R^4$ may be connected to each other and form a ring together with the carbon atom to which $R^3$ and $R^4$ are bonded.

Examples of the "ring" that $R^3$ and $R^4$ are connected to each other and form together with the carbon atom to which $R^3$ and $R^4$ are bonded can include a cyclopropane ring, a cyclobutane ring, a cyclopentane ring, a cyclohexane ring, a cycloheptane ring, a tetrahydrofuran ring, and a tetrahydropyran ring.

Preferably, the "ring" that $R^3$ and $R^4$ are connected to each other and form together with the carbon atom to which $R^3$ and $R^4$ are bonded is a cyclopentane ring, a cyclohexane ring, or a tetrahydropyran ring.

$R^5$ represents a hydrogen atom or a C1-6 alkyl group which is unsubstituted or has a substituent.

Examples of the "C1-6 alkyl group" in $R^5$ and a group which has a substituent in the "C1-6 alkyl group" can include the same groups as those exemplified in $X^1$. Preferably, $R^5$ is a hydrogen atom.

B represents an oxygen atom or a sulfur atom. Preferably, B is a sulfur atom.

$Q^2$ represents a C7-11 aralkyl group which is unsubstituted or has a substituent $X^2$, a C6-10 aryl group which is unsubstituted or has a substituent $X^2$, or a 5- or 6-membered heteroaryl group which is unsubstituted or has a substituent $X^2$. The number of the substituent $X^2$ on $Q^2$ is any integer of 1 to 5. When the number of the substituent $X^2$ is 2 or greater, $X^2$s may be the same as or different from each other.

A preferable number of the substituent $X^2$ is any integer of 1 and 2.

Examples of the "C7-11 aralkyl group" in $Q^2$ can include a benzyl group and a phenethyl group.

Examples of the "C6-10 aryl group" and the "5- to 6-membered heteroaryl group" in $Q^2$ can include the same groups as those exemplified in $Q^1$. Preferably, each of the "C6-10 aryl group" and the "5- to 6-membered heteroaryl group" in $Q^2$ is a phenyl group or a thienyl group.

Examples of the "C1-6 alkyl group", the "C2-6 alkenyl group", the "C2-6 alkynyl group", the "C3-8 cycloalkyl group", the "C1-6 alkoxy group", the "C1-7 acyl group", the "C1-6 alkoxycarbonyl group", the "amino group which has a substituent", the "C1-6 alkylthio group", the "C1-6 alkyl sulfonyl group", the "C6-10 aryl group", the "3- to 6-membered heterocyclic group", and the "halogeno group", in $X^2$, and a group having a substituent in these groups can include the same groups as those exemplified in $X^1$. Preferably, $X^2$ is a "C1-6 alkyl group", a "C1-6 alkoxy group", a "C1-6 haloalkyl group", a "C1-6 haloalkoxy group", or a "halogeno group".

According to the stereoisomerism of the double bond to which $R^5$ and B are bonded in Formula (I), the compound shows (E), (Z), or (E/Z). Here, the (E/Z) means a mixed state of an (E) steric configuration and a (Z) steric configuration, or a state in which the steric configuration is not specified. Specific examples of the stereoisomerism are represented by the following general formulas.

In Formulas (I-1) to (I-3), each of $Q^1$, A, $R^1$, $R^2$, $R^3$, $R^4$, n, $R^5$, B, and $Q^2$ has the same definition as that in Formula (I).

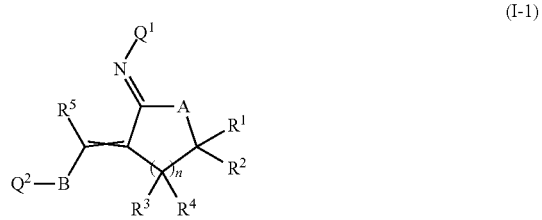

(I-1)

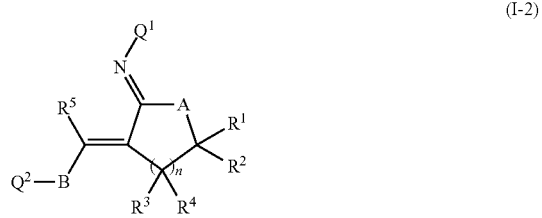

(I-2)

-continued

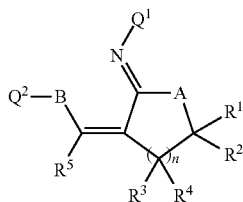
(I-3)

Among these, a compound having the steric configuration represent by Formula (I-2) is preferable. That is, the double bond moiety is preferably a compound having an (E) steric configuration.

In the ectoparasite control agent of the present invention, the 1-heterodiene compounds represented by Formula (I) are preferably the 1-heterodiene compounds represented by Formula (II).

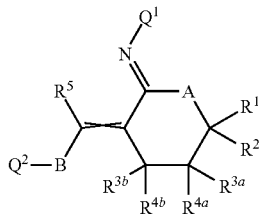
(II)

In Formula (II), each of $Q^1$, A, $R^1$, $R^2$, $R^5$, B, and $Q^2$ has the same definition as that in Formula (I).

Each of $R^{3a}$, $R^{3b}$, $R^{4a}$, and $R^{4b}$ independently represents a hydrogen atom, a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a C6-10 aryl group which is unsubstituted or has a substituent, a 3- to 6-membered heterocyclic group which is unsubstituted or has a substituent, a halogeno group, or a cyano group.

Examples of the "C1-6 alkyl group", the "C2-6 alkenyl group", the "C2-6 alkynyl group", the "C3-8 cycloalkyl group", the "C6-10 aryl group", the "3- to 6-membered heterocyclic group", and the "halogeno group", in $R^{3a}$, $R^{3b}$, $R^{4a}$, and $R^{4b}$, and a group having a substituent in these groups can include the same groups as those exemplified in $X^1$. Preferably, each of $R^{3a}$, $R^{3b}$, $R^{4a}$, and $R^{4b}$ independently is a hydrogen atom or a C1-6 alkyl group.

$R^{3a}$ and $R^{4a}$ may be connected to each other and form a ring together with the carbon atom to which $R^{3a}$ and $R^{4a}$ are bonded.

Examples of the "ring" that $R^{3a}$ and $R^{4a}$ are connected to each other and form together with the carbon atom to which $R^3$ and $R^4$ are bonded can include a cyclopropane ring, a cyclobutane ring, a cyclopentane ring, a cyclohexane ring, a cycloheptane ring, a tetrahydrofuran ring, and a tetrahydropyran ring.

Preferably, the "ring" that $R^3$ and $R^4$ are connected to each other and form together with the carbon atom to which $R^3$ and $R^4$ are bonded is a cyclopentane ring, a cyclohexane ring, or a tetrahydropyran ring.

According to the stereoisomerism of the double bond to which $R^5$ and B are bonded in Formula (II), the compound shows (E), (Z), or (E/Z). The double bond moiety is preferably a compound having an (E) steric configuration.

In the ectoparasite control agent of the present invention, the 1-heterodiene compounds represented by Formula (I) are more preferably the 1-heterodiene compounds represented by Formula (III).

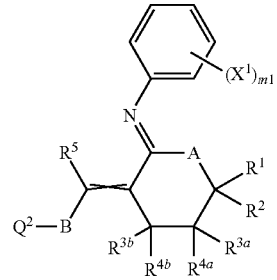
(III)

In Formula (III), each of $X^1$, A, $R^1$, $R^2$, $R^5$, B, and $Q^2$ has the same definition as that in Formula (I).

m1 represents any integer of 0 to 5. Preferably, m1 is any integer of 0 to 2.

Each of $R^{3a}$, $R^{3b}$, $R^{4a}$, and $R^{4b}$ independently represents a hydrogen atom, a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a C6-10 aryl group which is unsubstituted or has a substituent, a 3- to 6-membered heterocyclic group which is unsubstituted or has a substituent, a halogeno group, or a cyano group.

Examples of the "C1-6 alkyl group", the "C2-6 alkenyl group", the "C2-6 alkynyl group", the "C3-8 cycloalkyl group", the "C6-10 aryl group", the "3- to 6-membered heterocyclic group", and the "halogeno group", in $R^{3a}$, $R^{3b}$, $R^{4a}$, and $R^{4b}$, and a group having a substituent in these groups can include the same groups as those exemplified in $X^1$.

Preferably, each of $R^{3a}$, $R^{3b}$, $R^{4a}$, and $R^{4b}$ independently is a hydrogen atom or a C1-6 alkyl group.

$R^{3a}$ and $R^{4a}$ may be connected to each other and form a ring together with the carbon atom to which $R^{3a}$ and $R^{4a}$ are bonded.

Examples of the "ring" that $R^{3a}$ and $R^{4a}$ are connected to each other and form together with the carbon atom to which $R^3$ and $R^4$ are bonded can include a cyclopropane ring, a cyclobutane ring, a cyclopentane ring, a cyclohexane ring, a cycloheptane ring, a tetrahydrofuran ring, and a tetrahydropyran ring.

Preferably, the "ring" that $R^3$ and $R^4$ are connected to each other and form together with the carbon atom to which $R^3$ and $R^4$ are bonded is a cyclopentane ring, a cyclohexane ring, or a tetrahydropyran ring.

According to the stereoisomerism of the double bond to which $R^5$ and B are bonded in Formula (III), the compound shows (E), (Z), or (E/Z). The double bond moiety is preferably a compound having an (E) steric configuration.

The salt of the 1-heterodiene compound including a pharmaceutically acceptable salt and the usual method for preparing the salt are known in the related art. Examples of the salt include sulfuric acid, hydrochloric acid, phosphoric acid, tetrafluoroboronic acid, acetic acid, succinic acid, citric acid, lactic acid, maleic acid, fumaric acid, cholic acid, pamoic acid, mucic acid, glutamic acid, camphoric acid, glutaric acid, glycolic acid, phthalic acid, tartaric acid, formic acid, lauric acid, stearic acid, salicylic acid, methanesulfonic acid, benzenesulfonic acid, sorbic acid, picric acid, benzoic acid, cinnamic acid, and salts formed by standard reactions with both organic acids and inorganic acids such as the same acids, but the examples thereof are not limited thereto.

As the specific examples of the preparation method of the 1-heterodiene compounds, the preparation method described in PTLs 1 or 2 can be referred to.

The specific examples of the 1-heterodiene compounds capable of being synthesized by these preparation methods are shown in Tables 1 and 2. In Table 1, melting point (° C.), refractive index, or state (viscous oil state or amorphous state) are shown as physical property values. The symbols in Table 1 are the symbols in Formula (A). The symbols in Table 2 are the symbols in Formula (B).

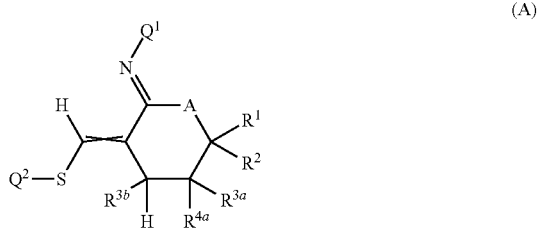

(A)

TABLE 1

| Compound No. | $Q^1$ | A | $R^1$ | $R^2$ | $R^{3a}$ | $R^{4a}$ | $R^{3b}$ | $Q^2$ | Steric configuration | Physical properties |
|---|---|---|---|---|---|---|---|---|---|---|
| 1-1 | 4-ClPh | S | =C(CH$_3$)$_2$ | | H | H | H | Ph | E | 101-103 |
| 1-2 | 4-CH$_3$Ph | S | Ph | H | H | H | H | Ph | E | 126-128 |
| 1-3 | 4-CH$_3$Ph | S | =CH$_2$ | | CH$_3$ | CH$_3$ | H | Ph | E | 82-84 |
| 1-4 | 4-ClPh | S | =CH$_2$ | | CH$_3$ | CH$_3$ | H | 4-FPh | E | 110-112 |
| 1-5 | 4-CH$_3$Ph | S | =CH$_2$ | | —(CH$_2$)$_5$— | | H | Ph | E | 117-119 |
| 1-6 | 4-CH$_3$Ph | S | =CH$_2$ | | CH$_3$ | CH$_3$ | H | 4-FPh | E | 79-82 |
| 1-7 | Ph | S | =CH$_2$ | | CH$_3$ | CH$_3$ | H | Ph | E | 91-94 |
| 1-8 | 4-CH$_3$Ph | S | =CH$_2$ | | —C$_2$H$_4$OC$_2$H$_4$— | | H | Ph | E | 134-136 |
| 1-9 | 4-CH$_3$Ph | S | =CH$_2$ | | —C$_2$H$_4$OC$_2$H$_4$— | | H | 4-FPh | E | 124-126 |
| 1-10 | 4-CH$_3$Ph | S | =CH$_2$ | | CH$_3$ | CH$_3$ | H | Thiophen-2-yl | E | 136-138 |
| 1-11 | 4-CH$_3$Ph | S | =CH$_2$ | | CH$_3$ | CH$_3$ | H | Thiophen-3-yl | E | 98-100 |
| 1-12 | 4-CH$_3$Ph | S | =CH$_2$ | | CH$_3$ | CH$_3$ | H | 5-CH$_3$-Thiophen-2-yl | E | 102-104 |
| 1-13 | 4-CH$_3$OPh | S | =CH$_2$ | | CH$_3$ | CH$_3$ | H | Thiophen-3-yl | E | 84-86 |
| 1-14 | 4-CH$_3$Ph | S | =CH$_2$ | | CH$_3$ | CH$_3$ | H | 2-FPh | E | 87-90 |
| 1-15 | 4-CH$_3$Ph | S | =CH$_2$ | | CH$_3$ | CH$_3$ | H | 4-CH$_3$Ph | E | 96-97 |
| 1-16 | 4-CH$_3$Ph | S | =CH$_2$ | | CH$_3$ | CH$_3$ | H | 4-ClPh | E | 96-97 |
| 1-17 | 4-CH$_3$Ph | S | =CH$_2$ | | CH$_3$ | CH$_3$ | H | Naphtalen-2-yl | E | 120-122 |
| 1-18 | 4-CH$_3$Ph | S | =CH$_2$ | | CH$_3$ | CH$_3$ | H | Naphtalen-1-yl | E | 124-125 |
| 1-19 | 4-CH$_3$Ph | S | =CH$_2$ | | CH$_3$ | CH$_3$ | H | 3-CH$_3$-Thiophen-2-yl | E | 107-108 |
| 1-20 | 4-CH$_3$Ph | S | =CH$_2$ | | CH$_3$ | CH$_3$ | H | 2-CH$_3$Ph | E | 71-74 |
| 1-21 | 4-CH$_3$Ph | S | =CH$_2$ | | CH$_3$ | CH$_3$ | H | 3-CH$_3$O-Thiophen-2-yl | E | 93-95 |
| 1-22 | 4-CH$_3$OPh | S | =CH$_2$ | | CH$_3$ | CH$_3$ | CH$_3$ | Ph | E | 96-98 |
| 1-23 | 4-CH$_3$Ph | S | =CH$_2$ | | CH$_3$ | CH$_3$ | H | 2,6-(CH$_3$)$_2$Ph | E | 122-124 |
| 1-24 | 4-CH$_3$Ph | S | =CH$_2$ | | CH$_3$ | CH$_3$ | H | 2,4-F$_2$-Ph | E | 82-84 |
| 1-25 | 4-CH$_3$Ph | S | =CH$_2$ | | CH$_3$ | CH$_3$ | H | 2-CH$_3$-Thiophen-3-yl | E | 83-85 |
| 1-26 | 4-CH$_3$Ph | S | CH$_3$ | CH$_3$ | H | H | H | Ph | E | 103-106 |
| 1-27 | 4-CH$_3$Ph | S | CH$_3$ | CH$_3$ | H | H | H | Thiophen-2-yl | E | 112-113 |
| 1-28 | 4-CH$_3$Ph | S | =CH$_2$ | | CH$_3$ | CH$_3$ | CH$_3$ | Ph | E | 133-135 |
| 1-29 | 4-CH$_3$Ph | S | =CH$_2$ | | CH$_3$ | CH$_3$ | CH$_3$ | Thiophen-2-yl | E | 138-141 |
| 1-30 | 4-CH$_3$Ph | S | =CH$_2$ | | CH$_3$ | CH$_3$ | H | 3,4-F$_2$Ph | E | 75-77 |
| 1-31 | 4-CH$_3$Ph | S | CH$_3$ | CH$_3$ | H | H | H | 3-CH$_3$Ph | E | 95-96 |
| 1-32 | 4-CH$_3$Ph | S | CH$_3$ | CH$_3$ | H | H | H | 2-FPh | E | 121-122 |
| 1-33 | 4-CH$_3$Ph | S | CH$_3$ | CH$_3$ | H | H | H | 2-CF$_3$Ph | E | 115-116 |
| 1-34 | Ph | S | H | H | CH$_3$ | CH$_3$ | H | Ph | E | 108-110 |
| 1-35 | Ph | S | H | H | CH$_3$ | CH$_3$ | H | Thiophen-2-yl | E | 107-110 |
| 1-36 | Ph | S | =CH$_2$ | | —(CH$_2$)$_4$— | | H | Ph | E | 65-67 |
| 1-37 | Ph | S | H | H | CH$_3$ | CH$_3$ | H | 4-FPh | E | 79-82 |
| 1-38 | 4-CH$_3$Ph | S | =CH$_2$ | | —(CH$_2$)$_4$— | | H | Thiophen-2-yl | E | 127-129 |
| 1-39 | 2,4-(CH$_3$)$_2$Ph | S | =CH$_2$ | | CH$_3$ | CH$_3$ | CH$_3$ | Thiophen-2-yl | E | 114-117 |
| 1-40 | 4-CH$_3$OPh | S | CH$_3$ | CH$_3$ | H | H | H | Ph | E/Z(5/1) | 89-91 |
| 1-41 | 4-CH$_3$OPh | S | CH$_3$ | CH$_3$ | H | H | H | Thiophen-2-yl | E/Z(5/3) | 95-98 |
| 1-42 | 4-CH$_3$Ph | S | =CH$_2$ | | CH$_3$ | CH$_3$ | CH$_3$ | Ph | E(BF$_4^-$ Salt) | 145-147 |
| 1-43 | 4-CH$_3$OPh | S | =CH$_2$ | | CH$_3$ | CH$_3$ | CH$_3$ | 2-CF$_3$Ph | E | 85-88 |
| 1-44 | 4-CH$_3$OPh | S | CH$_3$ | CH$_3$ | H | H | H | 3-CH$_3$Ph | E | 105-107 |
| 1-45 | 4-CH$_3$Ph | S | CH$_3$ | CH$_3$ | H | H | H | Bn | E | 144-147 |
| 1-46 | 4-CH$_3$Ph | O | CH$_3$ | CH$_3$ | H | H | H | 3-CH$_3$Ph | E | 79-80 |
| 1-47 | 4-CH$_3$Ph | O | CH$_3$ | CH$_3$ | H | H | CH$_3$ | 3-CH$_3$Ph | E | 130-132 |
| 1-48 | 4-ClPh | O | CH$_3$ | CH$_3$ | H | H | H | 3-CH$_3$Ph | E | 113-116 |
| 1-49 | 4-CH$_3$Ph | O | CH$_3$ | CH$_3$ | H | H | CH$_3$ | 4-FPh | E | 91-93 |
| 1-50 | 4-ClPh | O | CH$_3$ | CH$_3$ | H | H | H | Bn | E | 154-156 |
| 1-51 | 4-CF$_3$Ph | O | CH$_3$ | CH$_3$ | H | H | H | Ph | E | amorphous |
| 1-52 | 4-CF$_3$Ph | S | =C(CH$_3$)$_2$ | | H | H | CH$_3$ | Bn | E | 102-104 |
| 1-53 | 4-FPh | O | CH$_3$ | CH$_3$ | H | H | H | Ph | E | 106-108 |
| 1-54 | 3-CH$_3$Ph | S | CH$_3$ | CH$_3$ | H | H | H | Ph | E | amorphous |
| 1-55 | 3-CH$_3$Ph | S | CH$_3$ | CH$_3$ | H | H | H | 2,4-F$_2$-Ph | E | Viscous oil |
| 1-56 | 4-ClPh | S | CH$_3$ | CH$_3$ | H | H | H | 2,4-F$_2$-Ph | E | nD22.2 = 1.396 |
| 1-57 | 4-ClPh | S | CH$_3$ | CH$_3$ | H | H | H | 2-CF$_3$Ph | E | nD22.2 = 1.3058 |

TABLE 1-continued

| Compound No. | $Q^1$ | A | $R^1$ | $R^2$ | $R^{3a}$ | $R^{4a}$ | $R^{3b}$ | $Q^2$ | Steric configuration | Physical properties |
|---|---|---|---|---|---|---|---|---|---|---|
| 1-58 | 4-ClPh | S | $CH_3$ | $CH_3$ | H | H | H | 4-$CF_3$Ph | E | 106-108 |
| 1-59 | Ph | S | $CH_3$ | $CH_3$ | H | H | H | Ph | E | 90-91 |
| 1-60 | Ph | S | $CH_3$ | $CH_3$ | H | H | H | 4-FPh | E | amorphous |
| 1-61 | Ph | S | $CH_3$ | $CH_3$ | H | H | H | 3-$CH_3$Ph | E | 121-123 |
| 1-62 | Ph | S | $CH_3$ | $CH_3$ | H | H | H | Thiophen-2-yl | E | 120-121 |
| 1-63 | 4-FPh | S | $CH_3$ | $CH_3$ | H | H | H | 4-FPh | E | nD23.3 = 1.4411 |
| 1-64 | 4-FPh | S | $CH_3$ | $CH_3$ | H | H | H | 2,4-$F_2$-Ph | E | nD23.1 = 1.4067 |
| 1-65 | 4-FPh | S | $CH_3$ | $CH_3$ | H | H | H | 2-$CF_3$Ph | E | amorphous |
| 1-66 | 4-FPh | S | $CH_3$ | $CH_3$ | H | H | H | 4-$CF_3$Ph | E | nD23.3 = 1.4609 |
| 1-67 | 4-$CF_3$Ph | S | $CH_3$ | $CH_3$ | H | H | H | 4-FPh | E | amorphous |
| 1-68 | 4-$CF_3$Ph | S | $CH_3$ | $CH_3$ | H | H | H | 4-$CF_3$Ph | E | 102-104 |
| 1-69 | 4-$CH_3$Ph | S | =$CH_2$ | $CH_3$ | $CH_3$ | H | | Bn | E | 111-112 |
| 1-70 | 4-$CH_3$Ph | S | =$C(CH_3)_2$ | H | H | | $CH_3$ | Bn | E | 96-98 |
| 1-71 | 4-$CH_3$Ph | S | =$C(CH_3)_2$ | H | H | | $CH_3$ | 4-ClPhCH$_2$ | E | 115-118 |
| 1-72 | 4-$CH_3$OPh | S | =$C(CH_3)_2$ | H | H | | $CH_3$ | Bn | E | 81-83 |
| 1-73 | 4-$CH_3$OPh | S | =$CH_2$ | $CH_3$ | $CH_3$ | | $CH_3$ | Bn | E | 107-109 |
| 1-74 | 4-$CH_3$Ph | S | Et | Et | H | H | H | Bn | E | 103-105 |

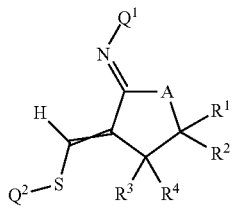

(B)

TABLE 2

| Compound No. | $Q^1$ | A | $R^1$ | $R^2$ | $R^3$ | $R^4$ | $Q^2$ | Steric configuration | Physical properties |
|---|---|---|---|---|---|---|---|---|---|
| 2-1 | 4-$CH_3$Ph | S | $CH_3$ | $CH_3$ | H | H | Ph | E | 102-103 |

[Ectoparasite Control Agent]

The ectoparasite control agent of the present invention contains at least one selected from the 1-heterodiene compounds according to the present invention and salts thereof (hereinafter, also referred to as the compound of the present invention) as an effective component.

The present invention provides a suppression method for an animal requiring suppression of parasite by ectoparasites, the suppression method including administration of an effective amount of at least one compound selected from the compounds of the present invention to the animal. The method may further include administration of at least one other effective component to the animal. The animal may be a mammal, a human or a pet such as a dog or a cat, a food animal such as cattle or sheep, or a fowl such as a chicken or a turkey.

The present invention provides a method for preventing or treating diseases infected through parasites, and includes administration of at least one compound selected from the compounds of the present invention to an animal in need thereof.

The present invention provides a method for suppressing harmful organisms, in which at least one compound selected from the compounds of the present invention acts on harmful organisms and/or the habitat thereof. The present invention provides a use of at least one compound selected from the compounds of the present invention for suppressing harmful organisms.

The present invention provides at least one compound selected from the compounds of the present invention used in treatment. The present invention further provides at least one compound selected from the compounds of the present invention, used for suppressing parasite by ectoparasites. In addition, the present invention provides a use of at least one compound selected from the compounds of the present invention for producing a formulation or a drug, which suppresses parasite by ectoparasites.

The parasites which are targets of the ectoparasite control agent of the present invention are mainly ectoparasites, and usually, harmful organisms such as insects and mites which are parasitic on or infect animals are exemplified, and an egg stage, a larval stage, a pupal stage, a nymph stage, and an adult stage thereof are included. In such harmful organisms, ticks, fleas, lice, mosquitoes, mites, beetles, and blood-sucking, biting, or harmful flies are included. The habitat of these harmful organisms is mainly the body surface of an animal. In the case of a horse fly, it is also present in the body.

The host animal for which the ectoparasite control agent of the present invention is effective may be a mammal, a fowl (turkey or chicken), or a non-mammal such as fish. In a case where the host animal is a mammal, the host animal may be a human or a mammal other than humans. Examples of the mammal other than humans include domestic animals such as livestock and a pet. Examples of the livestock include cattle, animals of camelidae, a pig, a sheep, a goat, and a horse. Examples of the pet include a dog, a rabbit, a cat, and other pets, which are breed and raised closely with humans as a part of the connection between humans and animals.

Examples of Acari which is a control target include the following pests.

(1) Mite belonging to Mesostigmata (a) Mite belonging to Dermanyssidae, for example, *Dermanyssus gallinae* of *Dermanyssus* spp.;

(b) Mite belonging to Macronyssidae, for example, *Ornithonyssus sylviarum*, *Ornithonyssus bursa*, and *Ornithonyssus bacoti* of *Ornithonyssus* spp;

(c) Mite belonging to Laelapidae, for example, *Laelaps echidninus* and *Laelaps jettmari* of *Laelaps* spp.; and for example, *Tropilaelaps clareae* and *Tropilaelaps koenigerum* of *Tropilaelaps* spp.; and (d) Mite belonging to Varroidae, for example, *Varroa destructor*, *Varroa jacobsoni*, and *Varroa underwoodi* of *Varroa* spp.

(2) Tick belonging to Metastigmata (a) Mite belonging to Argasidae, for example, *Argas persicus*, *Argas reflexus* of *Argas* spp.; and for example, *Ornithodoros moubata* of *Ornithodoros* spp.; and (b) Mite belonging to Ixodidae, for example, *Haemaphysalis concinna*, *Haemaphysalis punctata*, *Haemaphysalis cinnabarina*, *Haemaphysalis otophila*, *Haemaphysalis leachi*, *Haemaphysalis longicornis*, *Haemaphysalis mageshimaensis*, *Haemaphysalis yeni*, *Haemaphysalis campanulata*, *Haemaphysalis pentalagi*, *Haemaphysalis flava*, *Haemaphysalis megaspinosa*, *Haemaphysalis japonica*, and *Haemaphysalis douglasi* of *Haemaphysalis* spp.; for example, *Amblyomma americanum*, *Amblyomma variegatum*, *Amblyomma maculatum*, *Amblyomma hebraeum*, *Amblyomma cajennense*, and *Amblyomma testudinarium* of *Amblyomma* spp.; for example, *Ixodes ricinus*, *Ixodes hexagonus*, *Ixodes canisuga*, *Ixodes pilosus*, *Ixodes rubicundus*, *Ixodes scapularis*, *Ixodes holocyclus*, *Ixodes ovatus*, *Ixodes persulcatus*, and *Ixodes nipponensis* of *Ixodes* spp.; for example, *Rhipicephalus (Boophilus) microplus*, *Rhipicephalus (Boophilus) decoloratus*), *Rhipicephalus (Boophilus) annulatus*), and *Rhipicephalus (Boophilus) calceratus* of *Boophilus* spp.; for example, *Rhipicephalus evertsi*, *Rhipicephalus sanguineus*, *Rhipicephalus bursa*, *Rhipicephalus appendiculatus*, *Rhipicephalus capensis*, *Rhipicephalus turanicus*, and *Rhipicephalus zambeziensis* of *Rhipicephalus* spp.; and for example, *Dermacentor marginatus*, *Dermacentor reticulatus*, *Dermacentor pictus*, *Dermacentor albipictus*, *Dermacentor andersoni*, and *Dermacentor variabilis* of *Dermacentor* spp.

(3) Acaridida belonging to Astigmata (a) Mite belonging to Psoroptidae, for example, *Psoroptes ovis*, *Psoroptes cuniculi*, and *Psoroptes equi* of Psoroptidae spp.; for example, *Chorioptes bovis* of *Chorioptes* spp.; and *Otodectes cynotis* of *Otodectes* spp.;

(b) Mite belonging to Sarcoptidae, for example, *Sarcoptes scabiei*, *Sarcoptes canis*, *Sarcoptes bovis*, *Sarcoptes ovis*, *Sarcoptes rupicaprae*, *Sarcoptes equi*, and *Sarcoptes suis* of *Sarcoptes* spp.; and for example, *Notoedres cati* of *Notoedres* spp.; and (c) Mite belonging to Knemidokoptidae, for example, *Knemidokoptes mutans* of *Knemidokoptes* spp.

(4) Actinedida belonging to Prostigmata (a) Mite belonging to Demodixidae, for example, *Demodex canis*, *Demodex bovis*, *Demodex ovis*, *Demodex caprae*, *Demodex equi*, *Demodex caballi*, *Demodex suis*, and *Demodex cati* of *Demodex* spp.; and (b) Mite belonging to Trombiculidae, for example, *Trombicula alfreddugesi* and *Trombicula akamushi* of *Trombicula* spp.

Examples of Siphonaptera which is a control target include the following pests.

(a) Flea belonging to Tungidae, for example, *Tunga penetrans* of *Tunga* spp.;

(b) Flea belonging to Pulicidae, for example, *Ctenocephalides canis* and *Ctenocephalides felis* of *Ctenocephalides* spp.; for example, *Archaeopsylla erinacei* of *Archaeopsylla* spp.; for example, *Xenopsylla cheopis* of *Xenopsylla* spp.; for example, *Pulex irritans* of *Pulex* spp.; and for example, *Echidnophaga gallinacea* of *Echidnophaga* spp.;

(c) Flea belonging to Ceratophyllidae, for example, *Ceratophyllus gallinae* and *Ceratophyllus anisus* of *Ceratophyllus* spp.; and for example, *Nosopsyllus fasciatus* of *Nosopsyllus* spp.; and (d) Flea belonging to Leptopsyllidae, for example, *Leptopsylla segnis* of *Leptopsylla* spp.

When the compound of the present invention, the conjugate thereof, or the salt thereof is supplied, as a result of entering into the system of a harmful organism, or in the vicinity of the harmful organism, it is possible to suppress the harmful organism by the repellent action due to the presence of the compound of the present invention, the conjugate thereof, or the salt thereof. For the use on the body surface or in the body of an animal, the range of the compound of the present invention in the method, the conjugates thereof or the salts thereof is 0.01 mg/kg to 1000 mg/kg of the body weight of an animal, and more desirably 0.1 mg/kg to 100 mg/kg. The frequency of administration also depends on a plurality of factors, and it is possible to perform a single administration in the necessary period of time determined by an attending physician, a veterinarian, or another properly trained person. An additional effective component may be administered together with the compound of the present invention.

For example, for formulation components such as a salt, a carrier, and a raw material, the term "pharmaceutically acceptable" used in the application includes the meaning of "dermatologically acceptable" and "veterinarily acceptable", and therefore, includes an individual application to both humans and animals.

"Suppress" indicates that the parasites in the body or on the body surface of an animal host are decreased, eliminated, or prevented by administering at least one compound selected from the compounds of the present invention.

"Effective amount" indicates a sufficient amount of at least one compound selected from the compounds of the present invention to suppress parasites of ectoparasites, and includes reducing the number of ectoparasites to the extent capable of being measured, and it itself depends on a plurality of factors.

The present invention provides a formulation including a pharmaceutical formulation which includes at least one compound selected from the compounds of the present invention, and at least one acceptable carrier or an excipient system. The formulation may further include at least one additional effective component. The pharmaceutical formulation of the present invention may be a pharmaceutical formulation for humans or a pharmaceutical formulation for animals.

Examples of the additional effective component include the following compounds.

(1) Organo(thio)phosphate base: Acephate, azamethiphos, azinphos-methyl, azinphos-ethyl, bromophos-ethyl, bromfenvinphos, BRP, chlorpyrifos, chlorpyrifos-methyl, chlorpyrifos-ethyl, chlorfenvinfos, cadusafos, carbophenothion, chlorethoxyfos, chlormephos, coumaphos, cyanofenphos, cyanophos, CYAP, diazinon, dichlorvos, dicrotophos, dimethoate, disulfoton, demeton-S-methyl, dimethylvinphos, demeton-S-methylsulfone, dialifos, diazinon, dichlofenthion, dioxabenzophos, disulfoton, ethion, ethoprophos, etrimfos, EPN, fenamiphos, fenitrothion, fenthion, fensulfothion, flupyrazofos, fonofos, formothion, fosmethilan, heptenophos, isazophos, iodofenphos, isofenphos, isoxathion, iprobenfos, malathion, mevinphos, methamidophos, methidathion, monocrotophos, mecarbam, methacrifos, naled, omethoate, oxydemeton-methyl, paraoxon, parathion, parathion-methyl, phenthoate, phosalone, phosmet, phosphamidon, phorate, phoxim, pirimiphos-methyl, pirimiphos-ethyl, profenofos, prothiofos, fosthiazate, phosphocarb, propaphos, propetamphos, prothoate, pyridaphenthion, pyraclofos, quinalphos, salithion, sulprofos, sulfotep, tetrachlorvinphos, terbufos, triazophos, trichlorfon, tebupirimfos, temephos, thiometon, and vamidothion;

(2) Carbamate base: Alanycarb, aldicarb, bendiocarb, benfuracarb, carbaryl, carbofuran, carbosulfan, fenoxycarb, fenothiocarb, methiocarb, methomyl, oxamyl, pirimicarb, propoxur, thiodicarb, triazamate, ethiofencarb, fenobucarb, MIPC, MPMC, MTMC, pyridaphenthion, furathiocarb, XMC, aldoxycarb, allyxycarb, aminocarb, bendiocarb, bufencarb, butacarb, butocarboxim, butoxycarboxim, cloethocarb, dimetilan, formetanate, isoprocarb, metam-sodium, metolcarb, promecarb, thiofanox, trimethacarb, and xylylcarb;

(3) Pyrethroid base: Allethrin, bifenthrin, cyfluthrin, beta-cyfluthrin, cyhalothrin, lambda-cyhalothrin, cyphenothrin, cypermethrin, alpha-cypermethrin, beta-cypermethrin, zeta-cypermethrin, deltamethrin, esfenvalerate, ethofenprox, fenpropathrin, fenvalerate, imiprothrin, permethrin, prallethrin, pyrethrin, pyrethrin I, pyrethrin II, resmethrin, silafluofen, fluvalinate, tefluthrin, tetramethrin, tralomethrin, transfluthrin, profluthrin, dimefluthrin, acrinathrin, cycloprothrin, halfenprox, flucythrinate, bioallethrin, bioethanomethrin, biopermethrin, bioresmethrin, trans permethrin, empenthrin, fenfluthrin, fenpyrithrin, flubrocythrinate, flufenprox, flumethrin, metofluthrin, phenothrin, protrifenbute, piresmethrin, and terallethrin;

(4) Growth regulating substance:
(a) Chitin synthesis inhibitor: Chlorfluazuron, diflubenzuron, flucycloxuron, flufenoxuron, hexaflumuron, lufenuron, novaluron, teflubenzuron, triflumuron, bistrifluron, noviflumuron, buprofezin, hexythiazox, etoxazole, clofentezine, fluazuron, and penfluoron;
(b) Ecdysone antagonist: Halofenozide, methoxyfenozide, tebufenozide, chromafenozide, and azadirachtin;
(c) Juvenile hormone analogue: Pyriproxyfen, methoprene, diofenolan, epofenonane, hydroplane, kinoprene, and triprene; and
(d) Lipid biosynthesis inhibitor: Spirodiclofen, spiromesifen, spirotetramat, and flonicamid;

(5) Nicotine receptor agonist/antagonist compound: Acetamiprid, clothianidin, dinotefuran, imidacloprid, nitenpyram, thiacloprid, thiamethoxam, nithiazine, nicotine, bensultap, and cartap;

(6) GABA antagonistic compound:
(a) Acetoprole, ethiprole, fipronil, vaniliprole, pyrafluprole, and pyriprole; and
(b) Organochlorine base: Camphechlor, chlordane, endosulfan, HCH, γ-HCH, heptachlor, and methoxychlor;

(7) Macrocyclic lactone insecticide: Abamectin, emamectin benzoate, milbemectin, lepimectin, spinosad, ivermectin, selamectin, doramectin, epinomectin, and moxidectin;

(8) METI I compound: Fenazaquin, pyridaben, tebufenpyrad, tolfenpyrad, flufenerim, hydramethylnon, fenpyroximate, pyrimidifen, and dicofol;

(9) METI II and III compounds: Acequinocyl, fluacrypyrim, and rotenone;

(10) Uncoupling agent compound: Chlorfenapyr, binapacryl, dinobuton, dinocap, and DNOC;

(11) Oxidative phosphorylation inhibitor compound: Cyhexatin, diafenthiuron, fenbutatin-oxide, propargite, and azocyclotin;

(12) Ecdysis disturbance compound: Cyromazine;
(13) Mixed function oxidase inhibitor compound: Piperonyl butoxide;
(14) Sodium channel blocker compound: Indoxacarb and metaflumizone;
(15) Microbial pesticide: A BT agent, an insect pathogenic viral agent, an insect pathogenic filamentous fungus agent, a nematode pathogenic filamentous fungus agent; *bacillus* species, *beauveria bassiana, metarhizium anisopliae, paecilomyces* species, thuringiensin, and *verticillium* species;
(16) Latrophilin receptor agonist: Depsipeptide, cyclic depsipeptide, 24-membered cyclic depsipeptide, and emodepside;
(17) Octopamine agonist: Amitraz;
(18) Ryanodine derivative agonist: Flubendiamide, chlorantraniliprole, and cyantraniliprole;
(19) Inhibitor of magnesium stimulative ATPase: Thiocyclam, thiosultap, and nereistoxin;
(20) Feeding inhibitor: Pymetrozine;
(21) Mite growth inhibitor: Clofentezine and etoxazole;
(22) Others: Benclothiaz, bifenazate, pyridalyl, sulfur, cyenopyrafen, cyflumetofen, amidoflumet, tetradifon, chlordimeform, 1,3-dichloropropene, DCIP, phenisobromolate, benzomate, metaldehyde, spinetoram, pyrifluquinazon, benzoxymate, bromopropylate, chinomethionate, chlorobenzilate, chloropicrin, clothiazoben, dicyclanil, fenoxacrim, fentrifanil, flubenzimine, fluphenazine, gossyplure, japonilure, metoxadiazone, petroleum, potassium oleate, sulfluramid, tetrasul, triarathene, fluralaner, afoxolaner, 5-[5-(3,5-dichlorophenyl)-5-trifluoro-4,5-dihydroisoxal-3-yl]-2-(1H-1,2,4-triazol-1-yl)benzonitrile (CAS: 943137-49-3), and meta-diamides; and
(23) Anthelmintic
(a) Benzimidazole base: Fenbendazole, albendazole, triclabendazole, and oxibendazole;
(b) Salicylanilide base: Closantel and oxyclozanide;
(c) Substituted phenol base: Nitroxinil;
(d) Pyrimidine base: Pyrantel;
(e) Imidazothiazole base: Levamisole;
(f) tetrahydropyrimidine: Praziquantel; and
(g) Other anthelmintics: Cyclodiene, ryania, clorsulon, and metronidazole.

It is possible to mix at least one compound selected from the compounds of the present invention as a pharmaceutical composition for administration. The pharmaceutical composition for humans and mammals other than humans and the manufacturing step thereof are known in the related art. A formulation including an effective amount of at least one compound selected from the compounds of the present invention can be administered topically by a method in general use such as a dipping method, a spraying method, a liquid bath method, a pour-on method, a dropping method, and a scattering method. The term "topical application" is defined as applying to the body surface of an animal or a human, and includes skin or hair. This does not include an important systemic application such as a percutaneous application. At least one compound selected from the compounds of the present invention may be present in the formulation in an amount of 0.01% to 90% with respect to the total weight percent, in general. In addition, the formulation can contain other optional raw materials or carriers, and examples thereof include an antioxidant, a buffering agent, a preservative, a surfactant, a chelating agent, a wetting agent, an admixture, a UV-absorbing compound, a light stabilizer, a viscosity modifier, an antibacterial agent, a dye, a fragrance, a regulating agent, a deodorant, and a physiological or dermatologically acceptable diluent, an excipient, and an adjuvant. Such drugs are known in the related art. The formulation can also be administered by a parenteral administration such as injection (intramuscular, subcutaneous, intravenous, or intraperitoneal) or a cutaneous administration. To securely promote the stability and delivery of effective components, an additional effective component and carrier may be included in a formulation containing at least one compound selected from the compounds of the present invention.

The term "carrier" is used in the specification in order to describe optional raw materials other than the effective component in the formulation. The selection of the carrier widely depends on factors such as the specific method in the administration or application, the effect of the carrier on solubility and stability, and the properties of the dosage form.

The ectoparasite control agent of the present invention can control parasites over a long period of time in a single administration even in a case where the dosage is low, by excellent durability of activity that the compounds of the present invention have. Specifically, it is possible to control about three weeks to about one month in a single administration.

Therefore, the ectoparasite control agent of the present invention may be administered weekly, biweekly, monthly, or at a longer interval than those.

That is, when the ectoparasite control agent of the present invention is administered to a host animal, in particular, a warm-blooded animal by a known veterinary method, in particular, topically, a long validity period can be expected.

That is, the present invention further includes the following.

(1) An ectoparasite control agent, which is administered topically monthly or at a longer interval than that, contains at least one compound selected from the 1-heterodiene compounds represented by Formula (I) and salts thereof as an effective component.

(2) A method for controlling ectoparasites that are gathered in and on a warm-blooded animal, in which the ectoparasite control agent which contains at least one compound selected from the 1-heterodiene compounds represented by Formula (I) and salts thereof as an effective component is administered topically monthly or at a longer interval than that.

(3) A method for suppressing parasites in the body or on the body surface of an animal requiring suppression of parasite by parasites, in which an effective amount of at least one compound selected from the 1-heterodiene compounds represented by Formula (I) and salts thereof is administered topically to the animal monthly or at a longer interval than that.

(4) A topical use of at least one compound selected from the 1-heterodiene compounds represented by Formula (I) and salts thereof for suppressing parasite of ectoparasites monthly or at a longer interval than that.

Since the compounds shown below among 1-heterodiene compounds represented by Formula (I) show excellent durability of activity, a long validity period can be expected.

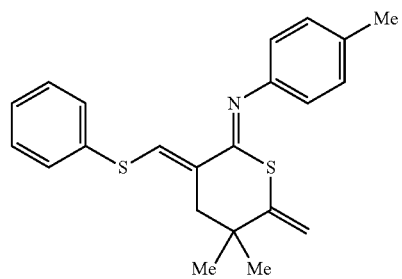

1-3

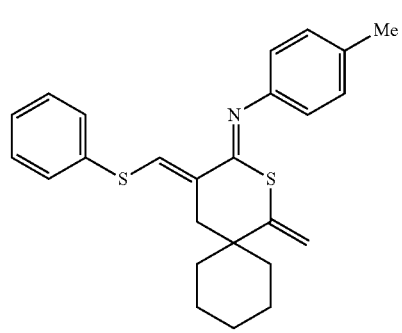

1-5

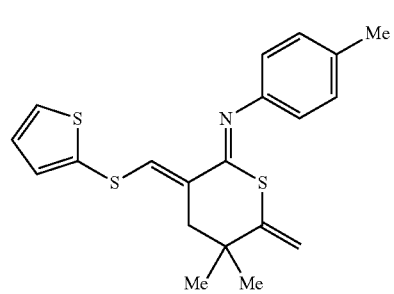

1-10

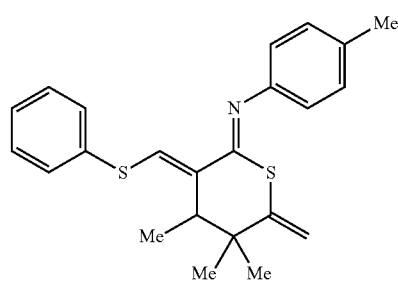

1-28

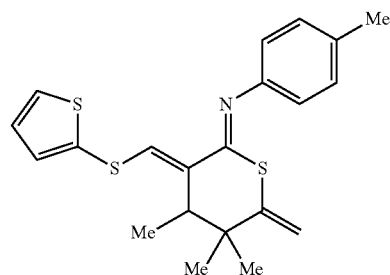

1-29

-continued

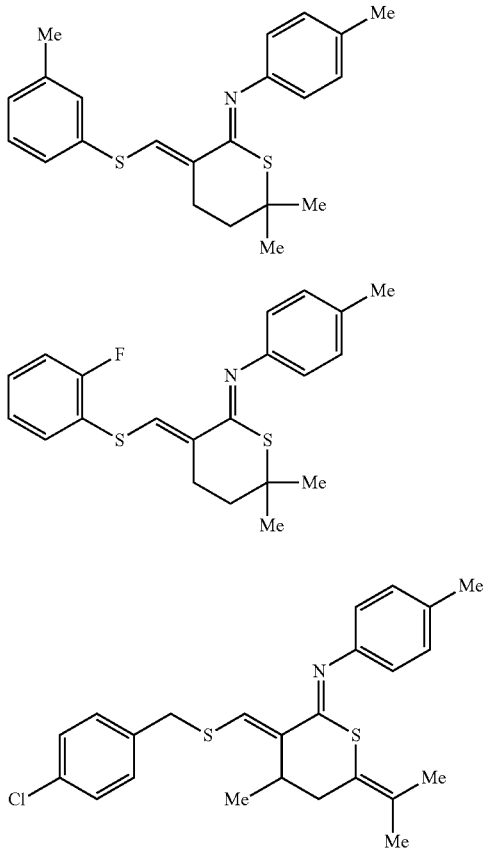

Test Example 1

Larval Immersion Microassay (LIM) In Vitro

Larval immersion microassay can be performed as described in "J. Med. Entomol. 41: 1034-1042 (2004)". In brief a test compound was mixed with dimethylsulfoxide (DMSO) to prepare a stock solution having a concentration of 10 mM. Then, a 10 mM sample solution was diluted with an aqueous solution containing 1% ethanol and 0.2% TritonX-100, per fraction using a 96-well microtiter plate to obtain 0.1 ml of a test compound having a desired concentration (in general, 0.3 mM or less) (dilution was repeated at least three times with respect to each compound or each concentration).

About 30 to 50 larvae of a lone star mite (*Amblyomma americanum*) were immersed in each well containing the test compound. After immersing for 30 minutes, the larvae were taken out using a wide bore pipette tip having a capacity of 0.05 ml, put into commercially available tissue biopsy bags made of paper, of which the upper portions were sealed with dialysis clips made of plastic, separately, and air-dried for 60 minutes in a state of being upside down.

Next, the bag containing the larvae was kept at a temperature of about 27° C. and a relative humidity of 90% or higher. After 24 hours, the bag was opened, and the surviving larvae and dead larvae were counted, and the mortality rate of the larvae was calculated.

The following test compounds showed an activity of 80% or greater in the test using this assay, at a concentration of 100 μM or less.

1-2, 1-3, 1-4, 1-5, 1-6, 1-7, 1-8, 1-9, 1-10, 1-15, 1-16, 1-17, 1-18, 1-19, 1-20, 1-21, 1-22, 1-23, 1-24, 1-25, 1-28, 1-29, 1-30, 1-31, 1-33, 1-36, 1-38, 1-39, 1-42, 1-43, 1-44, 1-45, 1-52, 1-69, 1-70, 1-71, 1-72, 1-73, 1-74, and 2-1

Test Example 2

Acaricidal Test of Rodent (RAT) In Vivo

Evaluation of the test compounds can be performed by a method obtained by modifying the analysis method described in "J. Med. Entomol. 43 (3) 526-532 (2006)". In the analysis method, other mite species (in references, described as a mite of *Amblyomma americanum*) can be also used, and, for example, other mite species such as a mite of *Dermacentor variabilis* can be also used.

A mite-holding unit (which was configured of small size nipples, a crew cap with a vent, and a reinforcing rubber washer) was attached to the back of an adult Sprague-Dawley rat. After attaching the holding unit, 0.05 ml of a test compound dissolved in acetone was applied topically on the skin surface inside the holding unit. After leaving to stand for a sufficient period of time to evaporate the acetone, about 10 American dog mites (*Dermacentor variabilis*) in nymph stage, to which food was not given, were put into each holding unit. Three to five rats per treatment group were used.

48 hours after the treatment, the holding unit was removed, and the surviving mites and dead mites were counted.

In the evaluation of efficacy, geometric mean calculation was used. First, the total number of surviving mites was converted by the natural logarithm transformation by adding 1 (Ln total number+1). That is, by adding 1 to each total number, the total number which was zero was adjusted. The geometric mean (GM) of the total number of mites in a treatment group was obtained by inverse-transforming the mean transformation value of the total number of treatment groups and subtracting 1. The non-treated control group was used for comparison with the groups in which the test compound was given for calculation of efficacy % (reduction % in the number of surviving mites). By comparing the geometric mean (GM) of surviving mites which were observed in the treated rats with the GM number of surviving mites which were counted in negative control rats, the efficacy of the treatment was calculated using the following equation.

Efficacy [%]=[(survival mites GM number of control–survival mites GM number of treatment groups)/(survival mites GM number of control)]×100

The following test compounds showed an efficacy of 50% or greater in the test using the analysis method, at an effective component concentration of 1% or less (10 mg/ml).

1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-46, 1-52, 1-55, 1-57, 1-61, 1-62, 1-64, 1-69, 1-71, 1-72, and 2-1

The activity in the above analysis method shows that the compound of the present invention is useful for suppressing parasite of mites.

Test Example 3

Parasite Extermination Test of Dog In Vivo

Each type of the test compounds was applied to four dogs. One day before treatment (−1 day) of the test compound, about 50 adults of *Rhipicephalus sanguineus* to which food was not given, per dog, were parasitized. It was estimated that 50% of the 50 ticks were male and 50% of the 50 ticks were female.

Separately, the tested compound was dissolved in a mixed solvent consisting of 80% by volume of benzyl alcohol and 20% by volume of isopropyl myristate such that the concentration became 50 mg/ml, whereby a test solution was prepared.

On zeroth day, several different spots of the interscapular region were treated with the test solution by "topical spot-on" such that the test compound was treated per 20 mg/kg per body weight of a dog. For comparison, a negative control was also prepared.

In order to evaluate the treatment against the parasitized ticks, survival of the ticks were observed on the 2nd day (48 hours after the treatment).

To evaluate the durability, on the 5th, 12th, 19th, and 28th day, 50 ticks to which food was not given, per dog, were parasitized again.

In addition, on the 12th and 28th day, 50 adult fleas (*Ctenocephalides felis*) to which food was not given were parasitized together.

Furthermore, on the 33rd day, 50 adult American dog mites (*Dermacentor variabilis*) to which food was not given were parasitized.

On the 7th, 14th, 21st, 30th and 35th day, 48 hours after each was parasitized, survival of the ticks and mites were observed, and the ticks and mites were removed from the dogs. The ticks were classified according to whether or not the ticks were attached, and the survival state was determined.

In the evaluation of efficacy, the same geometric mean calculation as that in Test Example 2 was used.

As the test compounds, 1-3, 1-5, 1-10, 1-28, 1-29, and 1-71 were used. Here, the test using American dog mites was performed on 1-28 and 1-71.

The test results are shown in the following table. The number of the upper portion of the cell in the table shows the average number of surviving parasites, and the lower portion shows the efficacy (%).

The efficacy in the above tests shows that the compound of the present invention is useful for suppressing parasite of ticks.

INDUSTRIAL APPLICABILITY

It is possible to provide an ectoparasite control agent containing at least one compound selected from the compounds represented by Formula (III) and salts thereof as an effective component.

The invention claimed is:

1. A method for suppressing parasites in the body or on the body surface of an animal requiring suppression of parasite by parasitic organisms,
wherein an effective amount of at least one compound selected from the 1-heterodiene compounds of Formula (I) and salts thereof is administered to the animal, wherein Formula (I) is:

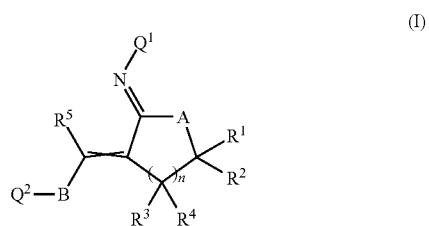

wherein, in Formula (I),
$Q^1$ represents a C6-10 aryl group which is unsubstituted or has a substituent $X^1$, or a 5- or 6-membered heteroaryl group which is unsubstituted or has a substituent $X^1$;
$X^1$ represents a C1-6 alkyl group which is unsubstituted or has a substituent, a C2-6 alkenyl group which is unsubstituted or has a substituent, a C2-6 alkenyl group which is unsubstituted or has a substituent, a C3-8 cycloalkyl group which is unsubstituted or has a sub-

TABLE 3

| | R. sanguineus | | | | | | D. variabilis | C. felis | |
|---|---|---|---|---|---|---|---|---|---|
| | 2nd day | 7th day | 14th day | 21st day | 30th day | 35th day | 14th day | 30th day |
| Untreated | 29.8(—) | 34.0(—) | 32.0(—) | 36.5(—) | 31.3(—) | 36.8(—) | 55.8(—) | 81.3(—) |
| 1-3 | 0.5(98.6%) | 0(100%) | 0(100%) | 0(100%) | 6.0(92.3%) | | 0(100%) | 0(100%) |
| 1-5 | 0(100%) | 0(100%) | 0(100%) | 1.8(95.4%) | 6.5(86.8%) | | 0(100%) | 8.8(98.2%) |
| 1-10 | 0.5(98.9%) | 0(100%) | 0(100%) | 0.5(99.5%) | 4.3(95.4%) | | 0(100%) | 0(100%) |
| 1-28 | 0.25(99.3%) | 0(100%) | 0(100%) | 0(100%) | 1.8(97.8) | 7.0(88.3%) | 0(100%) | 0(100%) |
| 1-29 | 1.3(97.3%) | 0(100%) | 0(100%) | 0(100%) | 0(100%) | | 0(100%) | 0(100%) |
| 1-71 | 5.0(90.%) | 0(100%) | 0(100%) | 1.8(96.9%) | 0(86.8%) | 9.8(80.3%) | 0(100%) | 0(100%) |

In addition, for Test Compound 1 to 32, the test compounds were treated per 5 mg/kg per body weight of an individual with respect to a dog. The test results are shown below.

TABLE 4

| | R. sanguineus | |
|---|---|---|
| | 2nd day | 5th day |
| Untreated | 29.0 (—) | 30.6 (—) |
| 1-32 | 0 (76.6%) | 0 (100%) | stituent, a hydroxyl group, a C1-6 alkoxy group which is unsubstituted or has a substituent, a C1-7 acyl group which is unsubstituted or has a substituent, a C1-6 alkoxycarbonyl group which is unsubstituted or has a substituent, an amino group which is unsubstituted or has a substituent, a C1-6 alkylthio group which is unsubstituted or has a substituent, a C1-6 alkylsulfonyl group which is unsubstituted or has a substituent, a C6-10 aryl group which is unsubstituted or has a substituent, a 3- to 6-membered heterocyclic group which is unsubstituted or has a substituent, a halogeno group, a cyano group, or a nitro group;

the number of the substituent X¹ on Q¹ is any integer of 1 to 5; and when the number of the substituent X¹ is 2 or greater, X¹s may be the same as or different from each other;

A represents an oxygen atom or a sulfur atom;

each of R¹ and R² independently represents a hydrogen atom, a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a C6-10 aryl group which is unsubstituted or has a substituent, a 3- to 6-membered heterocyclic group which is unsubstituted or has a substituent, or a cyano group;

an exomethylene group which is unsubstituted or has a substituent maybe formed by R¹ and R² being taken together;

each of R³ and R⁴ independently represents a hydrogen atom, a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a C6-10 aryl group which is unsubstituted or has a substituent, a 3- to 6-membered heterocyclic group which is unsubstituted or has a substituent, a halogeno group, or a cyano group;

n represents the number of methylene substituted with R³ and R⁴, and is any integer of 1 to 4; and when n is 2 or greater. R³ and R⁴ may be the same as or different from each other;

R³ and R⁴ may be connected to each other and form a ring together with the carbon atom to which R³ and R⁴ are bonded;

R⁵ represents a hydrogen atom or a C1-6 alkyl group which is unsubstituted or has a substituent;

B represents an oxygen atom or a sulfur atom;

Q² represents a C7-11 aralkyl group which is unsubstituted or has a substituent X², a C6-10 aryl group which is unsubstituted or has a substituent X², or a 5- or 6-membered heteroaryl group which is unsubstituted or has a substituent X²;

X² represents a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a hydroxyl group, a C1-6 alkoxy group which is unsubstituted or has a substituent, a C1-7 acyl group which is unsubstituted or has a substituent, a C1-6 alkoxycarbonyl group which is unsubstituted or has a substituent, an amino group which is unsubstituted or has a substituent, a C1-6 alkylthio group which is unsubstituted or has a substituent, a C1-6 alkylsulfonyl group which is unsubstituted or has a substituent, a C6-10 aryl group which is unsubstituted or has a substituent, a 3- to 6-membered heterocyclic group which is unsubstituted or has a substituent, a halogeno group, a cyano group, or a nitro group;

the number of the substituent X² on Q² is any integer of 1-5; and when the number of the substituent X² is 2 or greater, X²s may be the same as or different from each other; and according to the stereoisomerism of the double bond to which R⁵ and B are bonded in Formula (I) the compound shows (E), (Z), or (E/Z).

2. The method according to claim 1, wherein at least one other effective component is administered to the animal.

3. The method according to claim 1, wherein the animal is a human.

4. The method according to claim 1, wherein the animal is a pet.

5. The method according to claim 4, wherein the pet is a dog or a cat.

6. The method according to claim 1, wherein the animal is livestock.

7. The method according to claim 1, wherein the parasite is a tick.

8. A method for suppressing insects and mites which are parasitic on or infect animals,
wherein at least one compound selected from the 1-heterodiene compounds and salts thereof according to Formula (I) acts on the insects and mites which are parasitic on or infect animals and/or the habitat thereof, wherein Formula (I) is:

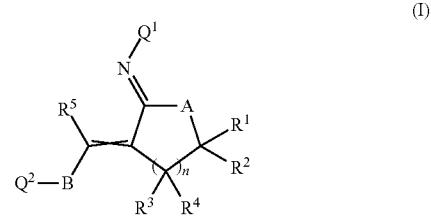

wherein, in Formula (I),

Q¹ represents a C6-10 aryl group which is unsubstituted or has a substituent X¹, or a 5- or 6-membered heteroaryl group which is unsubstituted or has a substituent X¹;

X¹ represents a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a hydroxyl group, a C1-6 alkoxy group which is unsubstituted or has a substituent a C1-7 acyl group which is unsubstituted or has a substituent, a C1-6 alkoxycarbonyl group which is unsubstituted or has a substituent, an amino group which is unsubstituted or has a substituent, a C1-6 alkylthio group which is unsubstituted or has a substituent, a C1-6 alkylsulfonyl group which is unsubstituted or has a substituent, a C6-10 aryl group which is unsubstituted or has a substituent, a 3- to 6-membered heterocyclic group which is unsubstituted or has a substituent, a halogeno group, a cyano group, or a nitro group;

the number of the substituent X¹ on Q¹ is any integer of 1 to 5; and when the number of the substituent X¹ is 2 or greater, X¹s may be the same as or different from each other;

A represents an oxygen atom or a sulfur atom:

each of R¹ and R² independently represents a hydrogen atom, a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent a C6-10 aryl group which is unsubstituted or has a substituent, a 3- to 6-membered heterocyclic group which is unsubstituted or has a substituent, or a cyano group;

an exomethylene group which is unsubstituted or has a substituent may be formed by $R^1$ and $R^2$ being taken together;

each of $R^3$ and $R^4$ independently represents a hydrogen atom, a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a C6-10 aryl group which is unsubstituted or has a substituent, a 3- to 6-membered heterocyclic group which is unsubstituted or has a substituent, a halogeno group, or a cyano group;

n represents the number of methylene substituted with $R^3$ and $R^4$, and is any integer of 1 to 4; and when n is 2 or greater, $R^3$ and $R^4$ may be the same as or different from each other;

$R^3$ and $R^4$ may be connected to each other and form a ring together with the carbon atom to which $R^3$ and $R^4$ are bonded;

$R^5$ represents a hydrogen atom or a C1-6 alkyl group which is unsubstituted or has a substituent;

B represents an oxygen atom or a sulfur atom;

$Q^2$ represents a C7-11 aralkyl group which is unsubstituted or has a substituent $X^2$, a C6-10 aryl group which is unsubstituted or has a substituent $X^2$, or a 5- or 6-membered heteroaryl group which is unsubstituted or has a substituent $X^2$;

$X^2$ represents a C1-6 alkyl group which is unsubstituted or has a substituent, a C2-6 alkenyl group which is unsubstituted or has a substituent, a C2-6 alkynyl group which is unsubstituted or has a substituent, a C3-8 cycloalkyl group which is unsubstituted or has a substituent, a hydroxyl group, a C1-6 alkoxy group which is unsubstituted or has a substituent, a C1-7 acyl group which is unsubstituted or has a substituent, a C1-6 alkoxycarbonyl group which is unsubstituted or has a substituent, an amino group which is unsubstituted or has a substituent, a C1-6 alkylthio group which is unsubstituted or has a substituent, a C1-6 alkylsulfonyl group which is unsubstituted or has a substituent, a C6-10 aryl group which is unsubstituted or has a substituent, a 3- to 6-membered heterocyclic group which is unsubstituted or has a substituent, a halogeno group, a cyano group, or a nitro group;

the number of the substituent $X^2$ on $Q^2$ is any integer of 1-5; and when the number of the substituent $X^2$ is 2 or greater, $X^2$s may be the same as or different from each other; and according to the stereoisomerism of the double bond to which $R^5$ and B are bonded in Formula (I), the compound shows (E), (Z), or (E/Z).

9. The method according to claim 8, wherein the habitat is an animal.

\* \* \* \* \*